(12) United States Patent
Savage

(10) Patent No.: US 11,286,276 B2
(45) Date of Patent: *Mar. 29, 2022

(54) CATIONIC STEROIDAL ANTIMICROBIALS

(71) Applicant: Paul B. Savage, Mapleton, UT (US)

(72) Inventor: Paul B. Savage, Mapleton, UT (US)

(73) Assignee: Brigham Young University, Provo, UT (US)

( * ) Notice: Subject to any disclaimer, the term of this patent is extended or adjusted under 35 U.S.C. 154(b) by 108 days.

This patent is subject to a terminal disclaimer.

(21) Appl. No.: 15/481,884

(22) Filed: Apr. 7, 2017

(65) Prior Publication Data

US 2017/0210776 A1 Jul. 27, 2017

Related U.S. Application Data

(62) Division of application No. 14/602,071, filed on Jan. 21, 2015, now abandoned.

(60) Provisional application No. 61/930,580, filed on Jan. 23, 2014, provisional application No. 61/945,681, filed on Feb. 27, 2014.

(51) Int. Cl.
*C07J 41/00* (2006.01)

(52) U.S. Cl.
CPC .................. *C07J 41/0088* (2013.01)

(58) Field of Classification Search
CPC .................................................. C07J 41/0088
See application file for complete search history.

(56) References Cited

U.S. PATENT DOCUMENTS

| | | |
|---|---|---|
| 821,187 A | 5/1906 | Peters |
| 3,843,779 A | 10/1974 | Norfleet |
| 4,248,236 A | 2/1981 | Linder |
| 4,284,236 A | 8/1981 | Bradshaw |
| 4,289,755 A | 9/1981 | Dhabhar |
| 4,296,206 A | 10/1981 | Simons |
| 4,473,988 A | 10/1984 | Scott |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 5,919,183 A | 7/1999 | Field |
| 6,117,332 A | 9/2000 | Hatch et al. |
| 6,143,738 A | 11/2000 | Zasloff |
| 6,217,896 B1 | 4/2001 | Benjamin |
| 6,228,393 B1 | 5/2001 | DiCosmo et al. |
| 6,329,488 B1 | 12/2001 | Terry et al. |
| 6,344,184 B1 | 2/2002 | Rolla |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,030 B2 | 10/2004 | De et al. |
| 6,803,066 B2 | 10/2004 | Traeder |
| 6,824,044 B1 | 11/2004 | Lapstun et al. |
| 6,872,303 B2 | 3/2005 | Knapp et al. |
| 6,872,306 B2 | 3/2005 | Shen |
| 6,939,376 B2 | 7/2005 | Shulze et al. |
| 7,226,577 B2 | 6/2007 | Cappelletti et al. |
| 7,235,552 B1 | 6/2007 | Hesse et al. |
| 7,282,214 B2 | 10/2007 | Wilcox et al. |
| 7,381,439 B2 | 6/2008 | Hilgren et al. |
| 7,481,973 B2 | 1/2009 | Beilfuss et al. |
| 7,598,234 B2 | 10/2009 | Savage et al. |
| 7,611,692 B2 | 11/2009 | Cappelletti et al. |
| 7,659,061 B2 | 2/2010 | Hendl et al. |

(Continued)

FOREIGN PATENT DOCUMENTS

| | | |
|---|---|---|
| CA | 2322847 A1 | 9/1999 |
| CA | 2640584 A1 | 8/2007 |

(Continued)

OTHER PUBLICATIONS

Berge et al., Pharmaceutical salts. Journal of Pharmaceutical Sciences, vol. 66(1), pp. 1-19 (Year: 1977).*
Bush, "Staphylococcal Infections", Merck Manuals Professional Edition, http://www.merckmanuals.com/professional/infectious-diseases/gram-positive-cocci/staphylococcal-infections.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.

(Continued)

*Primary Examiner* — Barbara P Badio
(74) *Attorney, Agent, or Firm* — Workman Nydegger

(57) ABSTRACT

Disclosed herein are cationic steroidal antimicrobials ("CSA compounds" or "ceragenins") and methods of making the same. Particularly advantageous methods are identified for the synthesis of CSA compounds. CSA compounds may be formulated for treating subjects with ailments responsive to CSA compounds, including but not limited to treating bacterial infections. Accordingly, some embodiments include formulations and methods of administering CSA compounds.

28 Claims, No Drawings

(56) References Cited

U.S. PATENT DOCUMENTS

| | | |
|---|---|---|
| 7,754,705 B2 | 7/2010 | Savage et al. |
| 7,850,947 B2 | 12/2010 | Cappelletti et al. |
| 7,854,941 B2 | 12/2010 | Urban et al. |
| 7,993,903 B2 | 8/2011 | Hayakawa et al. |
| 7,999,390 B2 | 8/2011 | Ishigaki et al. |
| 8,211,879 B2 | 7/2012 | Savage et al. |
| 8,420,050 B2 | 4/2013 | Cappelletti et al. |
| 8,444,954 B2 | 5/2013 | Cappelletti et al. |
| 8,529,681 B1 | 9/2013 | Hibbs et al. |
| 8,530,002 B1 | 9/2013 | Hibbs et al. |
| 8,557,031 B1 | 10/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,787,857 B2 | 7/2014 | Ezaki |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,180,132 B2 | 11/2015 | Fein et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 9,434,759 B1 | 9/2016 | Savage |
| 9,527,883 B2 | 12/2016 | Savage et al. |
| 9,533,063 B1 | 1/2017 | Savage |
| 9,546,195 B2 | 1/2017 | Savage |
| 9,603,859 B2 | 3/2017 | Genberg et al. |
| 10,226,550 B2 | 3/2019 | Savage et al. |
| 10,441,595 B2 | 10/2019 | Genberg et al. |
| 2002/0091278 A1 | 7/2002 | Savage et al. |
| 2002/0091433 A1 | 7/2002 | Ding et al. |
| 2002/0115121 A1 | 8/2002 | Garwin |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2003/0232791 A1 | 12/2003 | Levitt et al. |
| 2004/0009227 A1 | 1/2004 | Yao |
| 2004/0011358 A1 | 1/2004 | Smaldone et al. |
| 2004/0018154 A1 | 1/2004 | Pan et al. |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0014738 A1 | 1/2006 | Wachendorff-neumann et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0170563 A1 | 7/2007 | Chen |
| 2007/0190066 A1 | 8/2007 | Savage et al. |
| 2007/0190067 A1 | 8/2007 | Savage et al. |
| 2007/0190558 A1 | 8/2007 | Savage et al. |
| 2007/0243225 A1 | 10/2007 | McKay |
| 2007/0269375 A1 | 11/2007 | Chen et al. |
| 2008/0085949 A1 | 4/2008 | McGhee |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0024101 A1 | 1/2009 | Toshishige et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0124591 A1 | 5/2009 | Diamond et al. |
| 2009/0226884 A1 | 9/2009 | Tsujimoto et al. |
| 2009/0252781 A1 | 10/2009 | Sawhney et al. |
| 2009/0279944 A1 | 11/2009 | Schmitz et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0033540 A1 | 2/2011 | Daniloff et al. |
| 2011/0071099 A1 | 3/2011 | Bielawska et al. |
| 2011/0091376 A1 | 4/2011 | Savage et al. |
| 2011/0123624 A1 | 5/2011 | Zasloff |
| 2011/0135742 A1 | 6/2011 | Kim et al. |
| 2011/0171144 A1 | 7/2011 | Wang et al. |
| 2011/0230589 A1 | 9/2011 | Maggio et al. |
| 2012/0088733 A1 | 4/2012 | Kim et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0034500 A1 | 2/2013 | Savage et al. |
| 2013/0040265 A1 | 2/2013 | Park et al. |
| 2013/0089580 A1 | 4/2013 | Boutros |
| 2013/0137668 A1 | 5/2013 | Fein et al. |
| 2013/0234842 A1 | 9/2013 | Leitz |
| 2013/0236619 A1 | 9/2013 | Savage |
| 2013/0243823 A1 | 9/2013 | Genberg et al. |
| 2013/0243842 A1 | 9/2013 | Genberg et al. |
| 2013/0280312 A1 | 10/2013 | De Szalay |
| 2013/0280391 A1 | 10/2013 | Savage |
| 2014/0062960 A1 | 3/2014 | Kim et al. |
| 2014/0194401 A1 | 7/2014 | Genberg et al. |
| 2014/0219914 A1 | 8/2014 | Govindan et al. |
| 2014/0228905 A1 | 8/2014 | Bolea |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0203257 A1 | 7/2015 | Canegallo |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0374720 A1 | 9/2015 | Genberg et al. |
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0199390 A1 | 3/2016 | Beus et al. |
| 2016/0096864 A1 | 4/2016 | Savage |
| 2016/0193232 A1 | 7/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0232004 A1 | 8/2017 | Genberg et al. |
| 2017/0258963 A1 | 9/2017 | Savage et al. |
| 2018/0164221 A1 | 6/2018 | Singh et al. |
| 2018/0280550 A1 | 10/2018 | Savage |
| 2019/0076581 A1 | 3/2019 | Savage et al. |

FOREIGN PATENT DOCUMENTS

| | | |
|---|---|---|
| CA | 2842460 A1 | 1/2013 |
| CA | 2848567 A1 | 3/2013 |
| CA | 2888259 A1 | 4/2014 |
| CA | 2741177 C | 3/2018 |
| CN | 1236322 A | 11/1999 |
| CN | 101247838 A | 8/2008 |
| CN | 101378761 | 3/2009 |
| CN | 102145005 A | 8/2011 |
| CN | 102172356 | 9/2011 |

(56) References Cited

FOREIGN PATENT DOCUMENTS

| | | |
|---|---|---|
| CN | 104039369 A | 9/2014 |
| EP | 0341951 | 11/1989 |
| EP | 1208844 | 5/2002 |
| EP | 1219631 | 7/2002 |
| EP | 0832094 B1 | 2/2004 |
| EP | 1058552 B1 | 6/2004 |
| EP | 1311531 B1 | 5/2016 |
| JP | 60-080457 A | 5/1985 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002-515019 A | 5/2002 |
| JP | 2002255771 | 9/2002 |
| JP | 2002534532 | 10/2002 |
| JP | 2002538093 | 11/2002 |
| JP | 2004-506599 A | 3/2004 |
| JP | 2004506645 | 3/2004 |
| JP | 2009-131625 A | 6/2009 |
| JP | 2010-059194 A | 3/2010 |
| JP | 2010533051 | 10/2010 |
| JP | 2010538074 | 12/2010 |
| JP | 2011527702 | 11/2011 |
| JP | 2014500741 | 1/2014 |
| JP | 2014-520900 A | 8/2014 |
| JP | 2014-530191 A | 11/2014 |
| JP | 2017-519036 A | 7/2017 |
| WO | WO1995024415 | 9/1995 |
| WO | 98/05337 A1 | 2/1998 |
| WO | WO9827106 | 6/1998 |
| WO | 99/45024 A1 | 9/1999 |
| WO | WO1999044616 | 9/1999 |
| WO | WO2000042058 | 7/2000 |
| WO | WO2002014342 | 2/2002 |
| WO | WO2002067979 | 9/2002 |
| WO | WO2003015757 | 2/2003 |
| WO | 03/66119 | 8/2003 |
| WO | WO03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO2008048340 | 4/2008 |
| WO | 2008/096149 A2 | 8/2008 |
| WO | 2009049370 | 4/2009 |
| WO | WO 2008038965 | 4/2009 |
| WO | WO 2009079066 | 6/2009 |
| WO | 2009144708 | 12/2009 |
| WO | WO 2009/144708 A | 12/2009 |
| WO | WO2010006192 | 1/2010 |
| WO | WO2010036427 | 4/2010 |
| WO | WO2010062562 | 6/2011 |
| WO | WO2011066260 | 6/2011 |
| WO | WO2011109704 | 9/2011 |
| WO | WO2012061651 | 5/2012 |
| WO | 2013/013221 A1 | 1/2013 |
| WO | 2013/013223 A1 | 1/2013 |
| WO | WO2013029055 | 2/2013 |
| WO | WO2013029059 | 2/2013 |
| WO | 2013/040265 A1 | 3/2013 |
| WO | WO2013040269 | 3/2013 |
| WO | WO 2013109236 | 7/2013 |
| WO | 2013/131060 A1 | 9/2013 |
| WO | 2013/163359 A1 | 10/2013 |
| WO | 2013167743 | 11/2013 |
| WO | 2014062960 | 4/2014 |
| WO | 2014/107740 A2 | 7/2014 |
| WO | 2014/151411 A1 | 9/2014 |
| WO | 2015/058087 A1 | 4/2015 |
| WO | 2015/138716 A2 | 9/2015 |
| WO | 2015/200815 A1 | 12/2015 |
| WO | 2016/172543 A1 | 10/2016 |
| WO | 2016186821 | 11/2016 |
| WO | 2017/053355 A1 | 3/2017 |

OTHER PUBLICATIONS

International Search Report for PCT Application No. PCT/US2016/052771 dated Dec. 9, 2016.
Louw et al., "Recueil des Travaux Chimiques des Pays-Bas et la Belgique", vol. 73, pp. 667-676, 1954.
Martin, L., WebMD, 2012, pp. 1-25.
Novy et al., "Infections as a Cuase of Infertility", Glob. Libr. Women's med., (ISSN: 1756-2228) 2008; DOI 10.3843/GLOWM.10328.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO-Published Dec. 20, 2007).
Pycock, "The Dirty Mare", https://www.equine-reproduction.com/articles/DirtyMare.shtml, 2003.
U.S. Appl. No. 14/602,071, filed Jan. 21, 2015, Office Action dated Aug. 3, 2016.
U.S. Appl. No. 14/602,071, filed Jan. 21, 2015, Final Office Action dated Jan. 12, 2017.
U.S. Appl. No. 15/454,135, filed Mar. 9, 2017, Savage.
U.S. Appl. No. 15/585,632, filed May 3, 2017, Savage et al.
Alafort et al., "Lys and Arg in UBI: A specific site for a stable Tc-99m complex?", Nuclear Medicine and Biology 30 (2003) 605-615.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bakri et al., "Inhibitory effect of garlic extract on oral bacteria", Archives of Oral Biology, 50: 645-651.
Bellini et al., "Cholic and deoxycholic acids derivatives (Part I). Antimicrobial activity of cholane compounds", European J. of Medicinal Chem., 18(2), pp. 185-190, 1983.
Bellini et al., "Cholic and deoxycholic acids derivatives (Part II). Antimicrobial activity of cholane compounds", European J. of Medicinal Chem., 18(2), pp. 191-195, 1983.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al., "Imaging bacterial infection with 99mTc-ciprofloxacin (Infection)", Journal of Clinical Pathology, vol. 55, pp. 817-823, Apr. 6, 2015.
Brown, "Bioisosteres in Medicinal Chemistry, First Edition", edited by Nathan Brown, 2012, Ch. 2 Classical Bioisosteres, pp. 1-52.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al., "Antimicrobial Activities of Ceragenins against Clinical Isolates of Resistant *Staphylococcus aureas*", Antimicrobial Agents and Chemotherapy, vol. 51, No. 4, Apr. 2007, p. 1268-1273.
Clara et al., "Preclinical evaluation of magainin-A as a contraceptive antimicrobial agent", Fertility and Sterility 81 (5), pp. 1357-1365, 2004.
De Cuyper et al., "Surface functionalization of magnetoliposomes in view of improving iron oxide-based magnetic resonance imaging

(56) References Cited

OTHER PUBLICATIONS contrast agents: Anchoring of gadolinium ions to a lipophilic chelate", 2007 Anal. Biochem. 367: 266-273. Published online May 10, 2007.
Dörwald, "Side reactions in organic synthesis", 2005, Wiley-VCH Verlag GmbH & co., KGAA Weinheim, Preface. p. IX.
Epand et al., "Bacterial lipid composition and the antimicrobial efficacy of cationic steroid compounds (Ceragenins)", BBA, 2007, pp. 65-78.
Fichna et al., "Synthesis of Target-Specific Radiolabeled Peptides for Diagnostic Imaging", Bioconjugate Chem., 2003, 14, 3-17, American Chemical Society.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl_file/o10062704_sl.pdf.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2013/065510 dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Lankinen et al., "Ga-Dota-Peptide Targeting VAP-1 for In Vivo Evaluation of Inflammatory and Infectious Bone Conditions", 52nd Annual Meeting of the Orthopaedic Research Society.
Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Li et al., "Incremental conversion of Outer-Membrane Permeabilizers into Potent Antibiotics for Gram-Negative Bacteria", J. Am. Chem. Soc. 1999, 121, 931-940.
Lowe et al., "Effect of Hydrophobicity of a Drug on its Release from Hydrogels with Different Topological Structures" Journal of Polymer Science (1999) 73: 1031-1039 (9 pages).

Massoud et al., "Molecular imaging in living subjects: seeing fundamental biological processes in a new light", Genes & Development 17: 545-580 2003, Cold Spring Harbor Laboratory Press.
Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).
Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.
Roohi et al., Prepration, quality control and biological evaluation of 99m-Tc-labelled cationic steroid antibiotic (CSA-13), Radiochim. Acta 197, 57-62 (2009).
Paul B. Savage, et al: "Antibacterial Properties of cationic steroid antibiotics", FEMS Microbiology Letters, vol. 217, Nov. 2002, pp. 1-7.
Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Welling et al., "Radiochemical and biological characteristics of 99m-Tc-UBI 29-41 for imaging of bacterial infections", Nuclear Medicine and Biology 29 (2002) 413-422.
Willemen et al., "Miceli Formation and Antimicrobial Acivity of Cholic Acid Derivatives with three Permanent Ionic Head Groups", Angew. Chem. Int. Ed., 2002, 41, No. 22.
Williams et al., "In vivo efficacy of a silicone-cationic steroid antimicrobial coating to prevent implant-related infection", Biomaterials, Nov. 2012: 33(33): 8641-8656 (Department of Brigham Young University).
Winter et al., "Improved paragmentic chelate for molecular imaging with MRI", 2005 J. Magn. Magn. Mater. 293: 540-545.
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
U.S. Appl. No. 15/934,534, filed Mar. 23, 2018, Savage.
U.S. Appl. No. 15/895,848, filed Feb. 13, 2018, Genberg et al.
U.S. Appl. No. 15/926,534, filed Mar. 20, 2018, Savage.

(56) References Cited

OTHER PUBLICATIONS

U.S. Appl. No. 15/926,577, filed Mar. 20, 2018, Savage et al.
BASF, Pluronic® Block Copolymer NF Grades (Poloxamer NF Grades), Technical Bulletive (2004).
Belikov V.G., Pharmaceutical Chemistry, M., Higher School, 1993, p. 43-47.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Food definition, Merriam Webster, https://www.merriam-webster.com/dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824, 2002.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Lai, et al., "Controlled Released of a Bactericidal Ceragenin-Polymer Conjugate", September 227, 2006, p. 1, 46th Annual Interscience Conference on Antimicrobial Agents and Chemotherapy.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Papo et al., "Host peptides as new weapons in cancer treatment", CMLS Cell. Mol. Life Sci. 62 (2005), 784-785.
Piktel et al. Sporicidal Activity of Ceragenin CSA-13 Against Bacillus Subtillis, Scientific Reports, vol. 7, Mar. 15, 2017 [retrieved on Apr. 24, 2018. Retrieved from the internet: <URL: https://www.nature.com/articles/srep44452.pdf> Entire Document.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, p. 1-7.
International Search Report for PCT Application No. PCT/US2018/023566 dated Mar. 21, 2018.
Uncategorized: CSA Biotechnologies LLC, Apr. 5, 2011.
"Martindale: the complete drug reference, Cetrimide; Cetylpyridinium chloride Ed-Parfitt K", Jan. 1, 2000, pp. 1105-1106.
Barton, Journal of Clinical Investigation, vol. 118, No. 2, Feb. 2008, Review Series, pp. 413-420.
Chen et al, J Drug Target, Dec. 2012; 20(10):856-63, 892.
Ogata et al. Intramammary application of ozone therapy to acute clinical mastitis in dairy cows. J. Vet. Med. Sci. 62(7): 681-686, 2000.
De Haas et al. Associations between pathogen-specific cases of clinical mastitis and somatic cell count patterns. J. Dairy Sci. 87: 95-105.

"Mouth rinse" definition by Medical dictionay. Retrieved from http://medical-dictionary.thefreedictionary.com/mouth-i-rinse, 2009.
"Quaternary Ammoniuim Compounds", Van Nostrand's Scientific Encyclopedia, Jan. 1, 2006, John Wiley & Sons, Inc.
Ahmed, Hydrogel: Preparation, characterization, and applications: A review, Journal of Advanced Research (2015) 6: 105-121 (Year: 2015).
BASF, [Retrieved from internet <URL: https://worldaccount.basf.com/wa/NAFTA.about.en_US/Catalog/ChemicalsNAFTA-/doc4/BASF/PRD/30085231/.pdf?asset_type=pi/pdf&language=EN&urn=urn:documen-tum:eCommerce_sol_EU:09007bb280022b53.pdf >] (Year: 2004).
Bondaryk et al. Postep. Derm. Alergol., 2013, vol. 5, pp. 293-301.
csabiotech.com, Uncategorized: CSA Biotecfinologies LLC. posted by admin on Apr. 5, 2011 (Year: 2011).
Czemomysy-Furowicz et al. Etiological agents of mastitis in dairy cows on a farm in the West Pomeranian Region. Acta Sci. Pol., Zootechnica 7(1) 2008, 3-10.
Dean et al.; Flavor Associated with Fish Meal in Diets Fed to Broiler Chickens; 1968; Can. J. Animal Sci.; 49:11-15 (Year: 1968).
Deepak B. Salunke et al., "Amino Functionalized Novel Cholic Acid Derivatives Induce HIV-1 Replication and Syncytia Formation in T Cells", J. Med. Chem. 2006.
Ding, et al., "Correlation of the Antibacerial Activities of Cationic Peptid Antibiotics and Cationic Steroid Antibiotics", J. Med. Chem., vo. 45, pp. 663-669 (Year: 2002).
Dumortier, Get al. (Pharmaceutical Research, vol. 23, No. 12, Dec. 2006).
Feng, Theses Brigham Young University, BYU Scholars Archive, dated Dec. 19, 2011, 892.
Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.
Interational Search Report for PCT Application No. PCT/US2009/045485 dated Feb. 17, 2010.
International Search Report for PCT Application No. PCT/US2014/034986 dated Aug. 28, 2014.
Jacob; Feeding Fishmeal to Poultry; https://articles.extension.org/pages/67357/feeding-fishmeal-to-poultry; May 5, 2015; accessed Sep. 10, 2018 (Year: 2015).
K. Leszczynska et al., "Potential of ceragin CSA-13 and its mixture with pluronic F-127 as treatment of topical bacterial infections", Journal of Applied Microbiology, vol. 110, No. 1, Oct. 21, 2010, pp. 229-238.
Kaltsas et al., Endocrine-Related Cancer (2005) 12 683-699.
Leszczynska et al. (J Antimicrob Chemother, published Nov. 7, 2012), Bacterial activity of cationic lipids, pp. 1-9).
No author listed. Novel antibiotic coating shows potential for use on surgical implants. Healio website. Dec. 21, 2005. healio.com/orthopedics/news/online/%7BdcOe6031-1f10-4b3c-abf6-f50b9cfd683f%7D/novel-antibiotic-coating-shows-potential-for-use-on-surgical-implants. Accessed Jun. 2, 2019. (Year: 2005).
Notice of Allowance received for U.S. Appl. No. 14/257,776, dated Mar. 25, 2016.
Office Action received for U.S. Appl. No. 14/257,776, dated Apr. 16, 2015.
Opsenica D, et al., "Cholic Acid Derivatives as 1,2,4,5-Tetraoxane Carriers: Structure and Antimalarial and Antiproliferative Activity", J. Med Chern. Aug. 2000.
Oxford Dictionaries (on-line) definition of Adsorb ([Retrieved from internet <URL: http://www.oxforddictionaries.com/us/definition/american_english/adsorb >] [Downloaded Mar. 10, 2015]).
Perry et al., "Assessing peri-implant tissue infection prevention in a percutaneous model", Journal of Biomedical Materials Research Part B: Applied Biomaterials, vol. 028, Nov. 19, 2009, pp. 397-408.
Pollard et al. (J Antimicrob Chemother 2012; 67:2665-2672).
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Sigma-Aldrich, Poly(ethylene-co-vinyl acetate), [Retrieved from internet <URL: http://www.sigmaaldrich.com/catalog/product/aldrich/340502?lang=- en®ion=US >], [Downloaded Jul. 22, 2016], excerpt in action.

(56) References Cited

OTHER PUBLICATIONS

Staphylococcal Infections (Electronic Resource; Merck Manual). Retrieved on Jul. 3, 2017: [http://www.merckmanuals.com/professional/infectious-diseases/gram-positive-cocci/staphylococcal-infections].
U.S. Appl. filed Apr. 22, 2016, Savage et al., U.S. Appl. No. 15/135,900.
U.S. Appl. filed Apr. 22, 2016, Savage et al., U.S. Appl. No. 15/135,928.
U.S. Appl. filed Apr. 22, 2016, Savage et al., U.S. Appl. No. 15/135,969.
U.S. Appl. filed Apr. 23, 2015, Beus et al., U.S. Appl. No. 14/694,028.
U.S. Appl. filed Apr. 7, 2017, Savage., U.S. Appl. No. 15/481,184.
U.S. Appl. filed Aug. 19, 2015, Savage., U.S. Appl. No. 14/830,356.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Jul. 25, 2014, Savage, et al., U.S. Appl. No. 14/341,304.
U.S. Appl. filed Jun. 25, 2015, Genberg et al., U.S. Appl. No. 14/750,928.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 21, 2016, Beus et al., U.S. Appl. No. 15/076,313.
U.S. Appl. filed Mar. 23, 2018, Savage, Paul B., U.S. Appl. No. 15/934,534.
U.S. Appl. filed Oct. 16, 2014, Savage, et al., U.S. Appl. No. 14/515,858.
U.S. Appl. filed Oct. 30, 2014, Savage, et al., U.S. Appl. No. 14/398,094.
U.S. Appl. filed Oct. 6, 2015, Savage., U.S. Appl. No. 14/875,953.
U.S. Appl. filed Sep. 1, 2015, Genberg et al., U.S. Appl. No. 14/842,582.
U.S. Appl. filed Sep. 20, 2016, Genberg et al., U.S. Appl. No. 15/270,876.
U.S. Appl. filed Sep. 25, 2015, Savage., U.S. Appl. No. 14/866,213.
U.S. Appl. filed Sep. 9, 2015, Genberg et al., U.S. Appl. No. 14/848,819.
U.S. Appl. No. 13/841,549, filed Mar. 15, 2013, Office Action dated Apr. 23, 2015.
U.S. Appl. No. 14/288,126, filed May 27, 2014, Savage et al.
U.S. Appl. No. 14/341,304, filed Feb. 21, 2017, Final Office Action dated Feb. 21, 2017.
U.S. Appl. No. 14/926,738, filed Oct. 29, 2015, Vazquez et al.
U.S. Appl. No. 16/184,211, filed Nov. 8, 2018, Savage.
U.S. Application filed Feb. 17, 2015, by Savage, U.S. Appl. No. 14/624,200.
U.S. Application filed Mar. 10, 2015, by Darien et al., U.S. Appl. No. 14/642,905.
U.S. Application filed Jul. 29, 2014, by Vazquez et al., U.S. Appl. No. 14/364,283.
U.S. Application filed Oct. 25, 2016, by Vazquez et al., U.S. Appl. No. 15/333,514.
U.S. Appl. No. 13/288,902, filed Nov. 3, 2011, Notice of Allowance dated Aug. 9, 2013.
U.S. Patent Application filed Jul. 23, 2014 2014 by Vazquez et al., U.S. Appl. No. 14/339,342.
U.S. Patent Application filed Mar. 20, 2020, by Savage, U.S. Appl. No. 15/926,534.
U.S. Appl. filed Mar. 1, 2013, Savage., U.S. Appl. No. 13/783,007.
Valkonen, et al., "Bile acid amidoalcohols: simple orqanoqelators", Biosens Bioelectron, Dec. 2004.
Zaragoza Dorwald, Side Reactions in Organic Synthesis, 2005, WILEY-VCH Verlag GmbH & Co. KGaA, Weinheim, Preface. p. IX.
Dennison et al., "Anticancer a-Helical Peptides and Structure/Function Relationships Underpinning their Interactions with Tumour Cell Membranes", Current Protein and Peptide Science, 2006, 7, No. 6, pp. 1-13.
Ding, et al., "Origins of cell selectivity of cationic steroid antibiotics", Journal of American Chemical Society, Oct. 2004, pp. 13642-13648.
Examiner Interview Summary received for U.S. Appl. No. 14/208,082, dated Oct. 23, 2020, 4 pages.
International Search Report and Written Opinion received for PCT Patent Application No. PCT/US2020/034297, dated Aug. 26, 2020, 8 pages.
Kuroda, et al., "Ceragenin CSA-13 induces cell cycle arrest and antipro liferative effects in wild-type and p52 null mutant HCT116 colon cancer cells", Preclinical Report, Wolters Kluwer Health 2013.
Papo et al., "Host defense peptides as new weapons in cancer treatment", Cmls Cellular and Molecular Life Sciences, vol. 62, No. 7-8, Apr. 1, 2005, pp. 784-790.
Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Dumortier G, (A review of poloxamer 407 pharmaceutical and pharmacological characteristics. Pharm Res. Dec. 2006;23(12):2709-28. doi: 10.1007/S11095-006-9104-4. Epub Nov. 11, 2006. PMID: 17096184.).
Graterol et al., "Ultrastructural changes in premalignant and malignant lesions of the uterine cervix with papillomavirus infection", Journal of Cancer Research and Experimental Oncology, vol. 2, No. 3, Sep. 2010, pp. 35-42.
Hao et al., "A Phase I and Pharmacokinetic Study of Squalamine, an Aminosterol Angiogenesis Inhibitor", Clin Cancer Res, vol. 9, 2003, pp. 2465-2471.
Kwon, Ed., Polymeric Drug Delivery Systems, Taylor & Francis Group, LLC; pp. 1-653, 2005, pp. 350-351.
Lai XZ ( Ceragenins: cholic acid-based mimics of antimicrobial peptides. Acc Chern Res. Oct. 2008;41 (10): 1233-40. doi: 10.1021/ar700270t. Epub Jul. 11, 2008. PMID: 18616297.
Lawrence, Toby (The Nuclear Factor NF-?B Pathway in Inflammation, Cold Spring Harb Perspect Biol. Dec. 2009; 1(6): a001651).
McIntosh et al., "Towards Non-lnvasive Screening of Skin Lesions by Near-Infrared Spectroscopy", The Journal of Investigative Dermatology, vol. 116, No. 1, 2001, pp. 175-181.
Robert Bucki (Resistance of the antibacterial agent ceragenin CSA-13 to inactivation by DNA or F-actin and its activity in cystic fibrosis sputum, Journal of Antimicrobial Chemotherapy, vol. 60, Issue 3, Sep. 2007, pp. 535-545).
Schiller et al., "Potentiation of Platinum Antitumor Effects in Human Lung Tumor Xenografts by the Angiogenesis Inhibitor Squalamine: Effects on Tumor Neovascularization", Clin Cancer Res., vol. 5, 1999, pp. 4287-4294.

\* cited by examiner

CATIONIC STEROIDAL ANTIMICROBIALS

CROSS-REFERENCE TO RELATED APPLICATION

This application is a division of U.S. patent application Ser. No. 14/602,071, filed Jan. 21, 2015, which claims the benefit of U.S. Prov. App. No. 61/930,580, filed Jan. 24, 2014, and U.S. Prov. App. No. 61/945,681, filed Feb. 27, 2014, the disclosures of which are incorporated herein in their entirety.

BACKGROUND

Field of the Invention

The present application relates to the fields of pharmaceutical chemistry, biochemistry, and medicine. In particular, the present application relates to certain cationic steroidal antimicrobials ("CSA compounds" or "ceragenins").

Description of the Related Art

Endogenous antimicrobial peptides, such as the human cathelicidin LL-37, play key roles in innate immunity. LL-37 is found in airway mucus and is believed to be important in controlling bacterial growth in the lung. Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. However, clinical use of antimicrobial peptides presents significant issues including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display the same broad-spectrum antibacterial activity utilizing the same mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of antimicrobial peptides known, it is possible to categorize the structural features common to them. While the primary sequences of these peptides vary substantially, morphologies adopted by a vast majority are similar. Those that adopt alpha helix conformations juxtapose hydrophobic side chains on one face of the helix with cationic (positively charged) side chains on the opposite side. As similar morphology is found in antimicrobial peptides that form beta sheet structures: hydrophobic side chains on one face of the sheet and cationic side chains on the other.

Small molecule, non-peptide mimics of antimicrobial peptides, termed ceragenins or CSA compounds, have been developed. These compounds reproduce the amphiphilic morphology in antimicrobial peptides, represented above by CSA-13, and display potent, as well as diverse, biological activities (including, but not limited to anti-bacterial, anti-cancer, anti-inflammatory, promoting bone growth, promoting wound healing, etc.). Lead ceragenins can be produced at a large scale, and because they are not peptide based, they are not substrates for proteases. Consequently, the ceragenins represented an attractive compound class for producing pharmaceutically-relevant treatments.

SUMMARY OF THE INVENTION

Disclosed herein are compounds of Formula (I), or pharmaceutically acceptable salt thereof:

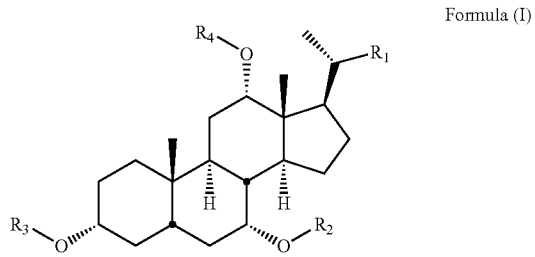

Formula (I)

wherein $R_1$ is selected from the group consisting of an optionally substituted $C_{11}$-$C_{22}$-alkylamino-$C_x$-alkyl; an optionally substituted $C_5$-$C_{22}$-alkylester-$C_x$-alkyl; and an optionally substituted $Z_1,Z_2$-amino-$C_x$-alkyl; $R_2$, $R_3$, and $R_4$, are independently selected from the group consisting of optionally substituted amino-$C_x$-alkyl and optionally substituted amino-$C_a$-alkylcarbonyl; x is 1-5; $Z_1$ and $Z_2$ are independently $C_6$-$C_{22}$-alkyl; and a is 2-5; with the proviso that when $R_2$, $R_3$, and $R_4$ are each unsubstituted amino-$C_3$-alkyl, $R_1$ is not unsubstituted $C_{16}$-alkylamino-$C_3$-alkyl; and with the proviso that when $R_2$, $R_3$, and $R_4$ are each the same unsubstituted amino-$C_{2-4}$-alkylcarbonyl, then $R_1$ is not unsubstituted $C_9$-alkylcarboxylic ester-$C_2$-alkyl; and with the proviso that when $R_2$, $R_3$, and $R_4$ are each unsubstituted amino-$C_3$-alkyl, then $Z_1$ and $Z_2$ are not both $C_x$-alkyl. Unless otherwise specified, the indicated number of carbon atoms in an "alkylcarbonyl" and in an "alkyl ester" that is an "alkylcarboxylic ester" is inclusive of the carbonyl carbon.

In some embodiments, $R_1$ is an optionally substituted $C_{11}$-$C_{22}$-alkylamino-$C_x$-alkyl; an optionally substituted $C_{11}$-alkylamino-$C_x$-alkyl; an optionally substituted $C_{12}$-alkylamino-$C_x$-alkyl; an optionally substituted $C_{13}$-alkylamino-$C_x$-alkyl; an optionally substituted Cia-alkylamino-$C_x$-alkyl; an optionally substituted $C_{15}$-alkylamino-$C_x$-alkyl; an optionally substituted $C_{16}$-alkylamino-$C_x$-alkyl, with the proviso that the $C_1$-$C_5$-alkyl is not $C_3$; an optionally substituted $C_{17}$-alkylamino-$C_x$-alkyl; an optionally substituted $C_{18}$-alkylamino-$C_x$-alkyl; an optionally substituted $C_{19}$-alkylamino-$C_x$-alkyl; an optionally substituted $C_{20}$-alkylamino-$C_x$-alkyl; an optionally substituted $C_{21}$-alkylamino-$C_x$-alkyl; an optionally substituted $C_{22}$-alkylamino-$C_x$-alkyl; an optionally substituted $C_{17}$-$C_{22}$-alkylamino-$C_x$-alkyl; and/or an optionally substituted $C_9$-$C_{22}$-alkylester-$C_x$-alkyl.

In some embodiments, $R_1$ is an optionally substituted $C_7$-alkylester-$C_x$-alkyl; an optionally substituted $C_x$-alkylester-$C_x$-alkyl; an optionally substituted $C_9$-alkylester-$C_x$-alkyl; an optionally substituted $C_{10}$-alkylester-$C_x$-alkyl; an optionally substituted $C_{11}$-alkylester-$C_x$-alkyl; an optionally substituted $C_{12}$-alkylester-$C_x$-alkyl; an optionally substituted $C_{13}$-alkylester-$C_x$-alkyl; an optionally substituted $C_{14}$-alkylester-$C_x$-alkyl; an optionally substituted $C_{15}$-alkylester- $C_x$-alkyl; an optionally substituted $C_{16}$-alkylester-$C_x$-alkyl; an optionally substituted $C_{17}$-alkylester-$C_x$-alkyl; an optionally substituted $C_{18}$-alkylester-$C_x$-alkyl; an optionally substituted $C_{19}$-alkylester-$C_x$-alkyl; an optionally substituted $C_{20}$-alkylester-$C_x$-alkyl; an optionally substituted $C_{21}$-alkylester-$C_x$-alkyl; and/or an optionally substituted $C_{22}$-alkylester-$C_x$-alkyl. In some embodiments the "ester" is a "carboxylic ester", such as an oxycarbonyl ester (i.e. —O—C(=O)—) or a carbonyloxy ester (i.e. —C(=O)—O—). In either case, the carbonyl carbon of the "carboxylic ester" is counted toward the total number of carbons in the "alkylester".

In some embodiments, $R_1$ is an optionally substituted $Z_1,Z_2$-amino-$C_x$-alkyl. In some embodiments, $Z_1$ and $Z_2$ are the same. In some embodiments, $Z_1$ and $Z_2$ are different. In some embodiments, $Z_1$ is $C_6$-alkyl; $C_7$-alkyl; $C_x$-alkyl (with the proviso that when $R_2$, $R_3$, and $R_4$ are amino-$C_3$-alkyl, $Z_2$ is not $C_x$-alkyl); $C_9$-alkyl; $C_{10}$-alkyl; $C_{11}$-alkyl; $C_{12}$-alkyl; $C_{13}$-alkyl; $C_{14}$-alkyl; $C_{15}$-alkyl; $C_{16}$-alkyl; $C_{17}$-alkyl; $C_{18}$-alkyl; $C_{19}$-alkyl; $C_{20}$-alkyl; $C_{21}$-alkyl; and/or $C_{22}$-alkyl. In some embodiments, $Z_2$ is $C_6$-alkyl; $C_7$-alkyl; $C_x$-alkyl (with the proviso that when $R_2$, $R_3$, and $R_4$ are amino-$C_3$-alkyl, $Z_1$ is not $C_x$-alkyl); $C_9$-alkyl; $C_{10}$-alkyl; $C_{11}$-alkyl; $C_{12}$-alkyl; $C_{13}$-alkyl; $C_{14}$-alkyl; $C_{15}$-alkyl; $C_{16}$-alkyl; $C_{17}$-alkyl; $C_{18}$-alkyl; $C_{19}$-alkyl; $C_{20}$-alkyl; $C_{21}$-alkyl; and/or $C_{22}$-alkyl.

In some embodiments x is 1, 2, 3, 4, and/or 5.

In some embodiments, $R_2$, $R_3$, and $R_4$ are the same. In some embodiments, $R_2$, $R_3$, and $R_4$ are different.

In some embodiments, a is 2, 3, 4, and/or 5.

In some embodiments, $R_2$, $R_3$, and $R_4$ are optionally substituted amino-$C_x$-alkyl and/or optionally substituted amino-$C_x$-alkylcarbonyl.

In some embodiments, one or more of $R_1$, $R_2$, $R_3$, and $R_4$ is not optionally substituted. In some embodiments, two or more of $R_1$, $R_2$, $R_3$, and $R_4$ are not optionally substituted. In some embodiments, three or more of $R_1$, $R_2$, $R_3$, and $R_4$ are not optionally substituted. In some embodiments, $R_1$, $R_2$, $R_3$, and $R_4$ are not optionally substituted. In some embodiments, $R_1$ is not optionally substituted. In some embodiments, $R_2$ is not optionally substituted. In some embodiments, $R_3$ is not optionally substituted. In some embodiments, $R_4$ is not optionally substituted.

Some embodiments disclosed herein are directed to a pharmaceutical composition comprising the compound of Formula I, or a pharmaceutically acceptable salt thereof, and a pharmaceutically acceptable excipient.

DETAILED DESCRIPTION

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Definitions

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements.

Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, the singular forms "a", "and," and "the" include plural referents unless the context clearly indicates otherwise. Thus, for example, reference to "a compound" or "a CSA" includes a plurality of compounds/CSAs and reference to "an infection" can include reference to one or more infections, and so forth.

As used herein, any "R" group(s) such as, without limitation, R', $R^2$, $R^3$, and $R^4$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond.

Whenever a group is described as being "optionally substituted" that group may be unsubstituted, or substituted with one, two, three or more of the indicated substituents, which may be the same or different, each replacing a hydrogen atom. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, alkylaminoalkyl, dialkylaminoalkyl, di(alkyl)aminoalkyl, cyanato, alkylaminoalkylaminoalkylamino, arylaminoalkyl, aminoalkyloxy, aminoalkyloxyalkyl, aminoalkylcarboxy, aminoalkylaminocarbonyl, aminoalkylcarboxamido, guanidinoalkyloxy, hydroxyalkyl and protected derivatives thereof. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "alkylthio" refers to the formula —SR wherein R is an alkyl as is defined above, such as "$C_{1-9}$ alkylthio" and the like, including but not limited to methylmercapto, ethylmercapto, n-propylmercapto, 1-methylethylmercapto (isopropylmercapto), n-butylmercapto, isobutylmercapto, sec-butylmercapto, tert-butylmercapto, and the like.

A "nitro" group refers to a "—$NO_2$" group.

A "cyanato" group refers to a "—OCN" group.

An "isocyanato" group refers to a "—NCO" group.

A "thiocyanato" group refers to a "—SCN" group.

An "isothiocyanato" group refers to a "—NCS" group.

A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to a "—$SO_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—$N(R_A)OC(=O)R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)$NR_AR_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N($R_A$)OC(=S)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N($R_A$)C(=O)$R_B$" group in which $R_A$ and $R_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

As used herein, "$C_a$" or "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

Unless otherwise specified, as used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 15 carbon atoms. The alkyl group could also be a lower alkyl having 1 to 6 carbon atoms. The alkyl group of the compounds may be designated as "$C_4$" or "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "$C_4$" or "$C_2$-$C_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "$C_4$" or "$C_2$-$C_4$ alkyl" or similar designations. An alkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group (although the definition of $C_6$-$C_{10}$ aryl covers the occurrence of "aryl" when no numerical range is designated). Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted.

Examples include but are not limited to benzyl, 2-phenylalkyl, 3-phenylalkyl, and naphthylalkyl.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl, and naphthylalkyl.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl, as defined herein. An O-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonamido" group refers to an "X$_3$CS(O)$_2$N(R$_A$)—" group wherein each X is a halogen, and R$_A$ hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl.

The term "azido" as used herein refers to a —N$_3$ group.

A "mercapto" group refers to an "—SH" group.

A "carbonyl" group refers to a C=O group.

"Lower alkylene groups" refer to a $C_1$-$C_{25}$ straight-chained alkyl tethering groups, such as —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—), and butylene (—CH$_2$CH$_2$CH$_2$CH$_2$—). A lower alkylene group can be substituted by replacing one or more hydrogen of the lower alkylene group with a substituent(s) listed under the definition of "substituted." As used herein, "cycloalkyl" refers to a completely saturated (no double or triple bonds) mono- or multicyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy (isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —NH$_2$ group.

As used herein, the term "hydroxy" refers to a —OH group.

A "cyano" group refers to a "—CN" group.

A "carbonyl" or an "oxo" group refers to a C=O group.

The term "azido" as used herein refers to a —N3 group.

As used herein, "aminoalkyl" refers to an amino group connected, as a substituent, via a lower alkylene group. Examples include H$_2$N-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

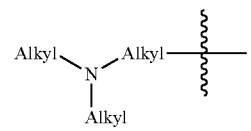

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include H$_2$N-alkyl-O— and H$_2$N-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include H$_2$N-alkyl-O-alkyl- and H$_2$N-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include H$_2$N-alkyl-C(=O)O— and H$_2$N-alkyl-O—C(=O)— with the term alkyl as defined herein.

As used herein, "aminoalkylaminocarbonyl" refers to an amino group connected, as a substituent, to an alkyl group connected, as a substituent, to an amino group connected, as a substituent, to a carbonyl group. Examples include H$_2$N-alkyl-NH—C(=O)— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include H$_2$N-alkyl-C(=O)—NH— with the term alkyl as defined herein.

As used herein, "guanidinoalkyloxy" refers to a guanidinyl group connected, as a substituent, to an alkyloxy group. Examples include

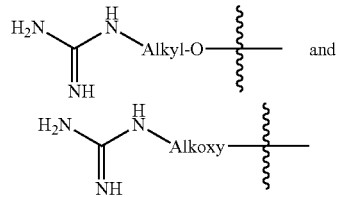

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

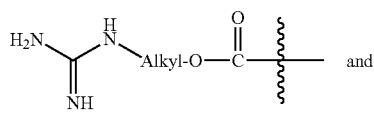

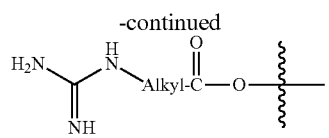

with the term alkyl as defined herein.

As used herein, "quaternary ammonium alkylcarboxy" refers to a quaternized amino group connected, as a substituent, to an alkyl group connected, as a substituent, to a carboxy group. Examples include

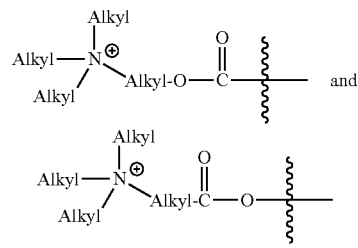

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA with a second CSA (which may be the same or different). An example of a linking group is (C$_1$-C$_{10}$) alkyloxy-(C$_1$-C$_{10}$) alkyl.

Commonly understand nomenclature and molecule representations are described and utilized throughout the specification. For example, a skilled artisan would readily appreciate that the following two structural representations are equivalent (wherein A, B, C, and D are unspecified functional groups):

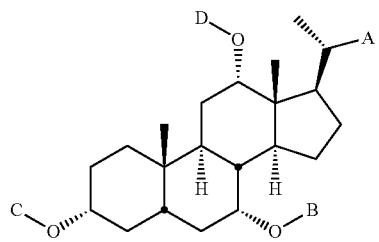

-continued

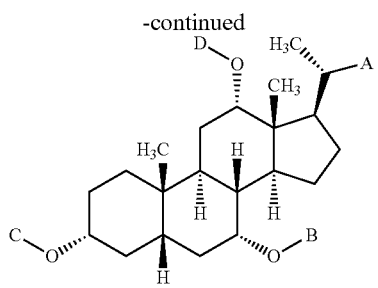

The terms "P.G." or "PG" or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein). Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.
Compounds:

Compounds useful in accordance with this disclosure are described herein, both generically and with particularity. The skilled artisan will recognize the compounds within the generic formula set forth herein and understand their preparation in view of the references cited herein and the Examples.

It has been discovered that alteration and optimization of CSA alkyl chain lengths can have pharmaceutically beneficial properties such as potent, as well as diverse, biological activities (including, but not limited to anti-bacterial, anti-cancer, anti-inflammatory, promoting bone growth, promoting wound healing, etc.), favorable solution stability, improved lipophilicity, and favorable elution from and stability in various polymers and hydrogels. Such properties are of critical concern for the handling and use of CSA compounds as pharmaceutical agents.

Some embodiments are directed to a compound of Formula (I), or pharmaceutically acceptable salt thereof:

Formula (I)

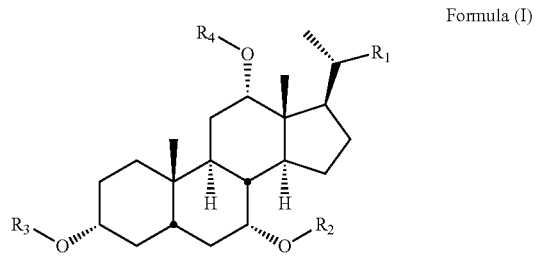

wherein $R_1$ is selected from the group consisting of an optionally substituted $C_{11}$-$C_{22}$-alkylamino-$C_x$-alkyl; an optionally substituted $C_8$-$C_{22}$-alkylester-$C_x$-alkyl; and an optionally substituted $Z_1,Z_2$-amino-$C_x$-alkyl; $R_2$, $R_3$, and $R_4$, are independently selected from the group consisting of optionally substituted amino-$C_x$-alkyl and optionally substituted amino-$C_a$-alkylcarbonyl; x is 1-5; $Z_1$ and $Z_2$ are independently $C_6$-$C_{22}$-alkyl; and a is 2-5; with the proviso that when $R_2$, $R_3$, and $R_4$ are each unsubstituted amino-$C_3$-alkyl, $R_1$ is not unsubstituted $C_{16}$-alkylamino-$C_3$-alkyl; and with the proviso that then $R_2$, $R_3$, and $R_4$ are each the same unsubstituted amino-$C_{2-4}$-alkylcarbonyl, then $R_1$ is not unsubstituted $C_9$-alkylcarboxylic ester-$C_2$-alkyl; and with the proviso that when $R_2$, $R_3$, and $R_4$ are each unsubstituted amino-$C_3$-alkyl, then $Z_1$ and $Z_2$ are not both $C_x$-alkyl. Unless otherwise specified, the indicated number of carbon atoms in an "alkylcarbonyl" and in an "alkyl ester" that is an "alkylcarboxylic ester" is inclusive of the carbonyl carbon.

In some embodiments, $R_1$ is an optionally substituted $C_{11}$-$C_{22}$-alkylamino-$C_x$-alkyl; an optionally substituted $C_1$-alkylamino-$C_x$-alkyl; an optionally substituted $C_{12}$-alkylamino-$C_x$-alkyl; an optionally substituted $C_{13}$-alkylamino-$C_x$-alkyl; an optionally substituted $C_{14}$-alkylamino-$C_x$-alkyl; an optionally substituted $C_{15}$-alkylamino-$C_x$-alkyl; an optionally substituted $C_{10}$-alkylamino-$C_x$-alkyl, with the proviso that the $C_1$-$C_5$-alkyl is not $C_3$; an optionally substituted $C_{17}$-alkylamino-$C_x$-alkyl; an optionally substituted $C_{18}$-alkylamino-$C_x$-alkyl; an optionally substituted $C_{19}$-alkylamino-$C_x$-alkyl; an optionally substituted $C_{20}$-alkylamino-$C_x$-alkyl; an optionally substituted $C_{21}$-alkylamino-$C_x$-alkyl; an optionally substituted $C_{22}$-alkylamino-$C_x$-alkyl; an optionally substituted $C_{17}$-$C_{22}$-alkylamino-$C_x$-alkyl; or an optionally substituted $C_9$-$C_{22}$-alkylester-$C_x$-alkyl. In some embodiments, $R_1$ is an optionally substituted $C_{11}$-$C_{22}$-alkylamino-$C_x$-alkyl. In some embodiments, $R_1$ is an optionally substituted $C_{11}$-alkylamino-$C_x$-alkyl. In some embodiments, $R_1$ is an optionally substituted $C_{12}$-alkylamino-$C_x$-alkyl. In some embodiments, $R_1$ is an optionally substituted $C_{13}$-alkylamino-$C_x$-alkyl. In some embodiments, $R_1$ is an optionally substituted $C_{14}$-alkylamino-$C_x$-alkyl. In some embodiments, $R_1$ is an optionally substituted $C_{15}$-alkylamino-$C_x$-alkyl. In some embodiments, $R_1$ is an optionally substituted $C_{16}$-alkylamino-$C_x$-alkyl, with the proviso that the $C_1$-$C_5$-alkyl is not $C_3$. In some embodiments, $R_1$ is an optionally substituted $C_{17}$-alkylamino-$C_x$-alkyl. In some embodiments, $R_1$ is an optionally substituted $C_{18}$-alkylamino-$C_x$-alkyl. In some embodiments, $R_1$ is an optionally substituted $C_{19}$-alkylamino-$C_x$-alkyl. In some embodiments, $R_1$ is an optionally substituted $C_{20}$-alkylamino-$C_x$-alkyl. In some embodiments, $R_1$ is an optionally substituted $C_{21}$-alkylamino-$C_x$-alkyl. In some embodiments, $R_1$ is an optionally substituted $C_{22}$-alkylamino-$C_x$-alkyl. In some embodiments, $R_1$ is an optionally substituted $C_{17}$-$C_{22}$-alkylamino-$C_x$-alkyl.

In some embodiments, $R_1$ is an optionally substituted $C_7$-alkylester-$C_x$-alkyl; an optionally substituted $C_x$-alkylester-$C_x$-alkyl; an optionally substituted $C_9$-alkylester-$C_x$-alkyl; an optionally substituted $C_{10}$-alkylester-$C_x$-alkyl; an optionally substituted $C_{11}$-alkylester-$C_x$-alkyl; an optionally substituted $C_{12}$-alkylester-$C_x$-alkyl; an optionally substituted $C_{13}$-alkylester-$C_x$-alkyl; an optionally substituted $C_{14}$-alkylester-$C_x$-alkyl; an optionally substituted $C_{15}$-alkylester-$C_x$-alkyl; an optionally substituted $C_{16}$-alkylester-$C_x$-alkyl; an optionally substituted $C_{17}$-alkylester-$C_x$-alkyl; an optionally substituted $C_{18}$-alkylester-$C_x$-alkyl; an optionally substituted $C_{19}$-alkylester-$C_x$-alkyl; an optionally substituted $C_{20}$-alkylester-$C_x$-alkyl; an optionally substituted $C_{21}$-alkylester-$C_x$-alkyl; and/or an optionally substituted $C_{22}$-alkylester-$C_x$-alkyl. In some embodiments, $R_1$ is an optionally substituted $C_{7-22}$-alkylester-$C_x$-alkyl; an optionally substituted $C_{8-22}$-alkylester-$C_x$-alkyl; an optionally substituted $C_{9-22}$-alkylester-$C_x$-alkyl; an optionally substituted $C_{10-22}$-alkylester-$C_x$-alkyl; an optionally substituted $C_{11-22}$-alkylester-$C_x$-alkyl; an optionally substituted $C_{12-22}$-alkylester-$C_x$-alky; an optionally substituted $C_{13-22}$-alkylester-$C_x$-alkyl; an optionally substituted $C_{14-22}$-alkylester-$C_x$-alkyl; an optionally substituted $C_{15-22}$-alkylester-$C_x$-alkyl; an optionally substituted $C_{16-22}$-alkylester-$C_x$-alkyl; an optionally substituted $C_{17-22}$-alkylester-$C_x$-alkyl; an optionally substituted $C_{18-22}$-alkylester-$C_x$-alkyl; an optionally substituted $C_{19-22}$-alkylester-$C_x$-alkyl; an optionally substituted $C_{20-22}$-alkylester-$C_x$-alkyl; or an optionally substituted $C_{21-22}$-alkylester-$C_x$-alkyl. In some embodiments, $R_1$ is an optionally substituted $C_{8-21}$-alkylester-$C_x$-alkyl; an optionally substituted $C_{8-20}$-alkylester-$C_x$-alkyl; an optionally substituted $C_{8-19}$-alkylester-$C_x$-alkyl; an optionally substituted $C_{8-18}$-alkylester-$C_x$-alkyl; an optionally substituted $C_{8-17}$-alkylester-$C_x$-alkyl; an optionally substituted $C_{8-16}$-alkylester-$C_x$-alkyl; an optionally substituted $C_{8-15}$-alkylester-$C_x$-alkyl; an optionally substituted $C_{8-14}$-alkylester-$C_x$-alkyl; an optionally substituted $C_{8-13}$-alkylester-$C_x$-alkyl; an optionally substituted $C_{8-12}$-alkylester-$C_x$-alkyl; an optionally substituted $C_{8-11}$-alkylester-$C_x$-alkyl; an optionally substituted $C_{8-10}$-alkylester-$C_x$-alkyl; or an optionally substituted $C_{8-9}$-alkylester-$C_x$-alkyl. In some embodiments the "ester" is a "carboxylic ester", such as an oxycarbonyl ester (i.e. —O—C(=O)—) or a carbonyloxy ester (i.e. —C(=O)—O—). In either case, the carbonyl carbon of the "carboxylic ester" is counted toward the total number of carbons in the "alkylester".

In some embodiments, $R_1$ is an optionally substituted $Z_1,Z_2$-amino-$C_x$-alkyl. In some embodiments, $Z_1$ and $Z_2$ are the same. In some embodiments, $Z_1$ and $Z_2$ are different. In some embodiments, $Z_1$ is $C_6$-alkyl; $C_7$-alkyl; $C_x$-alkyl (with the proviso that when $R_2$, $R_3$, and $R_4$ are amino-$C_3$-alkyl, $Z_2$ is not $C_x$-alkyl); $C_9$-alkyl; $C_{10}$-alkyl; CH-alkyl; $C_{12}$-alkyl; $C_{13}$-alkyl; $C_{11}$-alkyl; $C_{15}$-alkyl; $C_{16}$-alkyl; $C_{17}$-alkyl; $C_{15}$-alkyl; $C_{19}$-alkyl; $C_{20}$-alkyl; $C_2$ i-alkyl; and/or $C_{22}$-alkyl. In some embodiments, $Z_2$ is $C_6$-alkyl; $C_7$-alkyl; $C_x$-alkyl with the proviso that when $R_2$, $R_3$, and $R_4$ are amino-$C_3$-alkyl, $Z_1$ is not $C_x$-alkyl; $C_9$-alkyl; $C_{10}$-alkyl; CH-alkyl; $C_{12}$-alkyl; $C_{13}$-alkyl; $C_{11}$-alkyl; $C_{15}$-alkyl; $C_{16}$-alkyl; $C_{17}$-alkyl; $C_{15}$-alkyl; $C_{19}$-alkyl; $C_{20}$-alkyl; $C_{21}$-alkyl; and/or $C_{22}$-alkyl. In some embodiments, $Z_1$ is $C_6$-alkyl. In some embodiments, $Z_1$ is $C_7$-alkyl. In some embodiments, $Z_1$ is $C_x$-alkyl and with the proviso that when $R_2$, $R_3$, and $R_4$ are amino-$C_3$-alkyl, $Z_2$ is not $C_x$-alkyl. In some embodiments, $Z_1$ is $C_{10}$-alkyl. In some embodiments, $Z_1$ is $C_{11}$-alkyl. In some embodiments, $Z_1$ is $C_{12}$-alkyl. In some embodiments, $Z_1$ is $C_{13}$-alkyl. In some embodiments, $Z_1$ is $C_{14}$-alkyl. In some embodiments, $Z_1$ is $C_{15}$-alkyl. In some embodiments, $Z_1$ is $C_{16}$-alkyl. In some embodiments, $Z_1$ is Cr-alkyl. In some embodiments, $Z_1$ is $C_{18}$-alkyl. In some embodiments, $Z_1$ is $C_{19}$-alkyl. In some embodiments, $Z_1$ is $C_{20}$-alkyl. In some embodiments, $Z_1$ is $C_{21}$-alkyl. In some embodiments, $Z_1$ is $C_{22}$-alkyl. In some embodiments, $Z_2$ is $C_6$-alkyl. In some embodiments, $Z_2$ is $C_7$-alkyl. In some embodiments, $Z_2$ is $C_x$-alkyl with the proviso that when $R_2$, $R_3$, and $R_4$ are amino-$C_3$-alkyl, $Z_1$ is not $C_x$-alkyl. In some embodiments, $Z_2$ is $C_9$-alkyl. In some embodiments, $Z_2$ is $C_{10}$-alkyl. In some embodiments, $Z_2$ is $C_{11}$-alkyl. In some embodiments, $Z_2$ is $C_{12}$-alkyl. In some embodiments, $Z_2$ is $C_{13}$-alkyl. In some embodiments, $Z_2$ is $C_{14}$-alkyl. In some embodiments, $Z_2$ is $C_{15}$-alkyl. In some embodiments, $Z_2$ is $C_{16}$-alkyl. In some embodiments, $Z_2$ is $C_{17}$-alkyl. In some embodiments, $Z_2$ is $C_{15}$-alkyl. In some embodiments, $Z_2$ is $C_{19}$-alkyl. In some embodiments, $Z_2$ is $C_{20}$-alkyl. In some embodiments, $Z_2$ is $C_{21}$-alkyl. In some embodiments, $Z_2$ is $C_{22}$-alkyl. In some embodiments, $Z_1$ and $Z_2$ are independently $C_{6-22}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{7-22}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{8-22}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{9-22}$-alkyl. In some embodiments, $Z_1$ and $Z_2$ are independently $C_{10-22}$-alkyl. In some embodiments, $Z_1$ and $Z_2$ are independently $C_{11-22}$-alkyl. In some embodiments, $Z_1$ and $Z_2$ are independently $C_{12-22}$-alkyl. In some embodiments, $Z_1$ and $Z_2$ are independently $C_{15-22}$-alkyl. In some embodiments, $Z_1$ and $Z_2$ are independently $C_{14-22}$-alkyl. In some embodiments, $Z_1$ and $Z_2$ are independently $C_{15-22}$-alkyl. In some embodiments, $Z_1$ and $Z_2$ are independently $C_{16-22}$-alkyl. In some embodiments, $Z_1$ and $Z_2$ are independently $C_{17-22}$-alkyl. In some embodiments, $Z_1$ and $Z_2$ are independently $C_{18-22}$-alkyl. In some embodiments, $Z_1$ and $Z_2$ are independently $C_{19-22}$-alkyl. In some embodiments, $Z_1$ and $Z_2$ are independently $C_{20-22}$-alkyl. In some embodiments, $Z_1$ and $Z_2$ are independently $C_{21-22}$-alkyl. In some embodiments, $Z_1$ and $Z_2$ are independently $C_{6-21}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-20}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-19}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-18}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-17}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-16}$-alkyl, with the proviso that when $R_2$, $R_3$, and $R_4$ are amino-$C_3$-alkyl, $Z_1$ and $Z_2$ are not both $C_8$-alkyl. In some embodiments, $Z_1$ and $Z_2$ are independently $C_{6-15}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-14}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-13}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-12}$-alkyl, with the proviso that when $R_2$, $R_3$, and $R_4$ are amino-$C_3$-alkyl, $Z_1$ and $Z_2$ are not both $C_8$-alkyl. In some embodiments, $Z_1$ and $Z_2$ are independently $C_{6-11}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-10}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-9}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-8}$-alkyl, with the proviso that when $R_2$, $R_3$, and $R_4$ are amino-$C_3$-alkyl, $Z_1$ and $Z_2$ are not both $C_x$-alkyl. In some embodiments, $Z_1$ and $Z_2$ are independently $C_{6-7}$-alkyl.

In some embodiments x is 1, 2, 3, 4, and/or 5. In some embodiments, x is 1. In some embodiments, x is 2. In some embodiments, x is 3. In some embodiments, x is 4. In some embodiments, x is 5. In some embodiments, x is 1-4. In some embodiments, x is 1-3. In some embodiments, x is 1-2. In some embodiments, x is 2-5. In some embodiments, x is 3-5. In some embodiments, x is 4-5

In some embodiments, $R_2$, $R_3$, and $R_4$ are the same. In some embodiments, $R_2$, $R_3$, and $R_4$ are different.

In some embodiments, a is 2, 3, 4, and/or 5. In some embodiments, a is 2. In some embodiments, a is 3. In some embodiments, a is 4. In some embodiments, a is 5. In some embodiments, a is 2-5. In some embodiments, a is 3-5. In some embodiments, a is 4-5. In some embodiments, a is 2-4. In some embodiments, a is 2-3.

In some embodiments, $R_2$, $R_3$, and $R_4$ are optionally substituted amino-$C_x$-alkyl and/or optionally substituted amino-$C_x$-alkylcarbonyl.

In some embodiments, one or more of $R_1$, $R_2$, $R_3$, and $R_4$ is not optionally substituted. In some embodiments, two or more of $R_1$, $R_2$, $R_3$, and $R_4$ are not optionally substituted. In some embodiments, three or more of $R_1$, $R_2$, $R_3$, and $R_4$ are not optionally substituted. In some embodiments, $R_1$, $R_2$, $R_3$, and $R_4$ are not optionally substituted. In some embodiments, $R_1$ is not optionally substituted. In some embodiments, $R_2$ is not optionally substituted. In some embodiments, $R_3$ is not optionally substituted. In some embodiments, $R_4$ is not optionally substituted.

In some embodiments, the compound of Formula (I), or pharmaceutically acceptable salt thereof, is selected from the group consisting of:

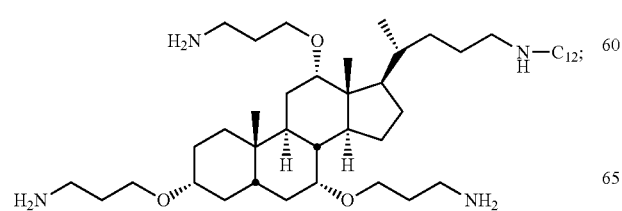

CSA-131

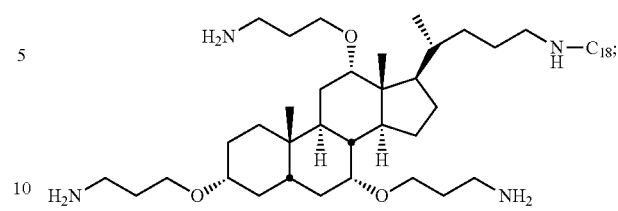

CSA-132

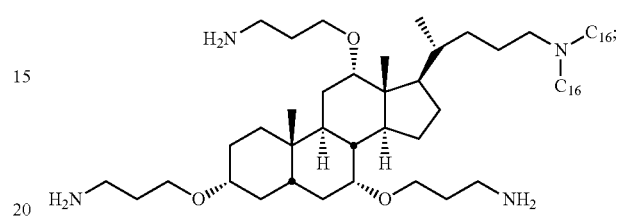

CSA-133

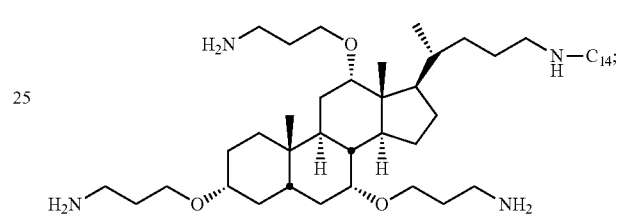

CSA-134

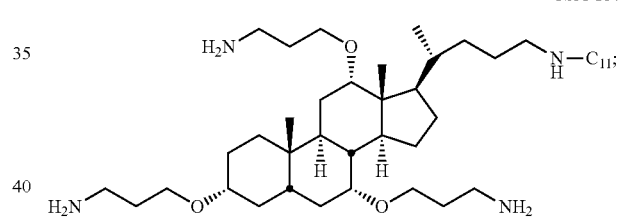

CSA-137

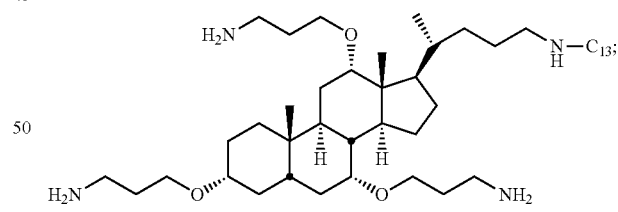

CSA-138

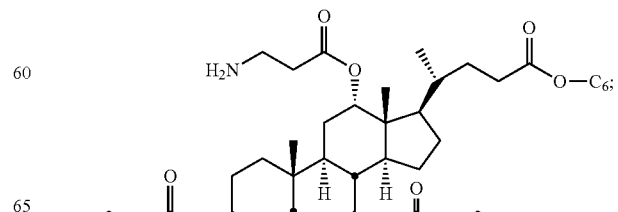

CSA-142

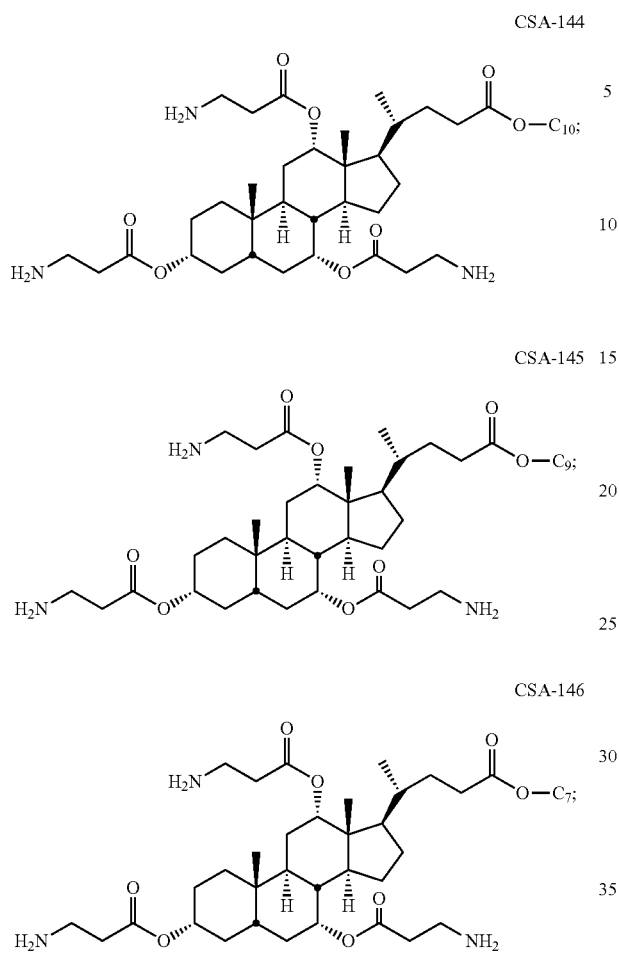
and pharmaceutically acceptable salts thereof, wherein $C_{xx}$ indicates a branched or linear alkyl group containing the indicated number (xx) of carbon atoms.
In some embodiments, the compound of Formula (I) is selected from the group consisting of:
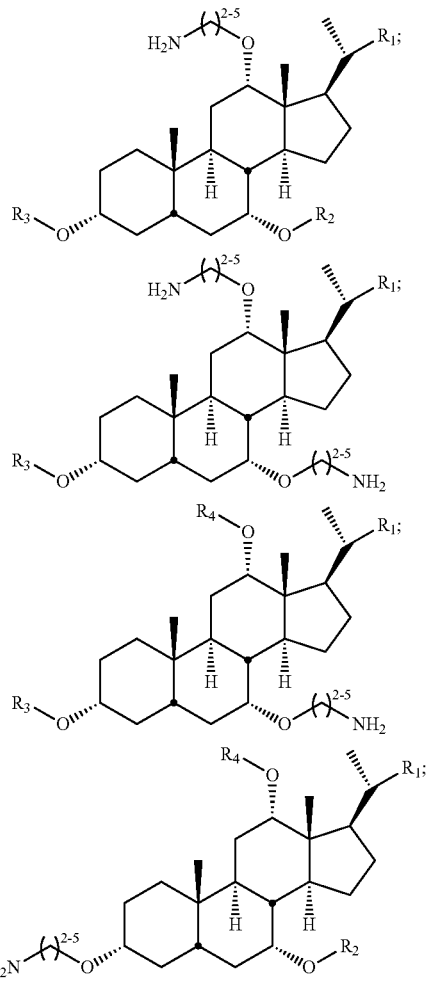
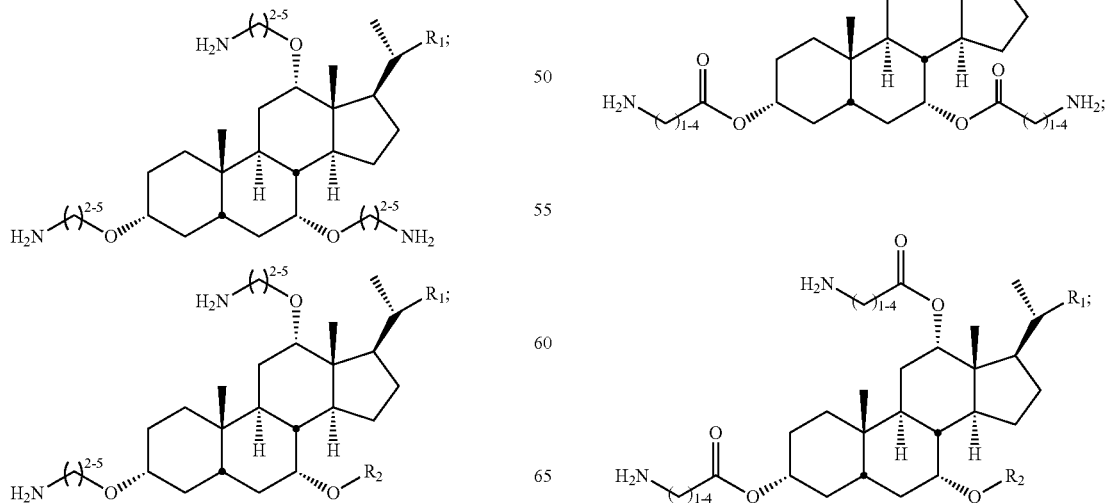

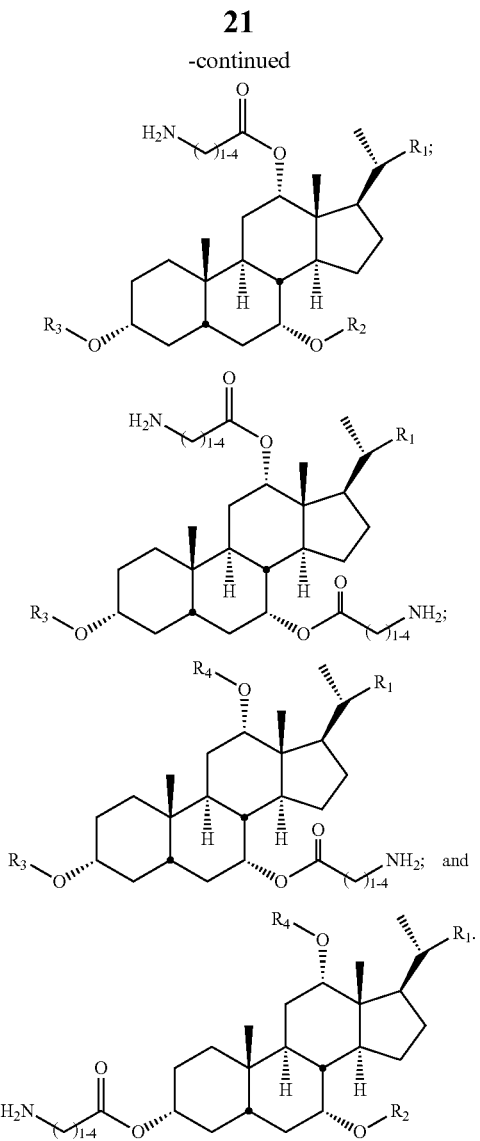
In some embodiments, the compound of Formula (I) is selected from the group consisting of:
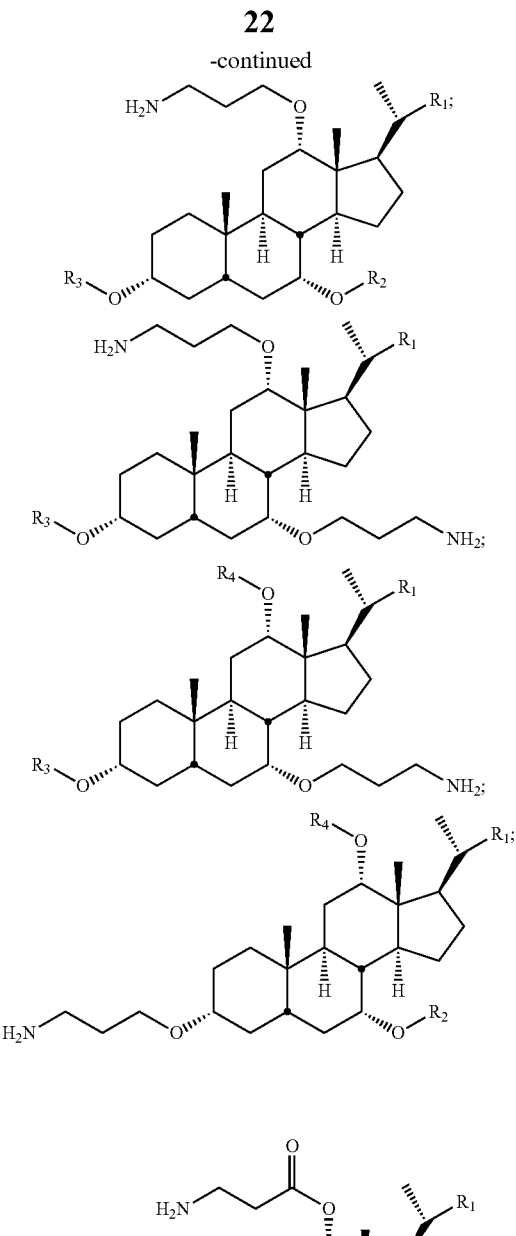
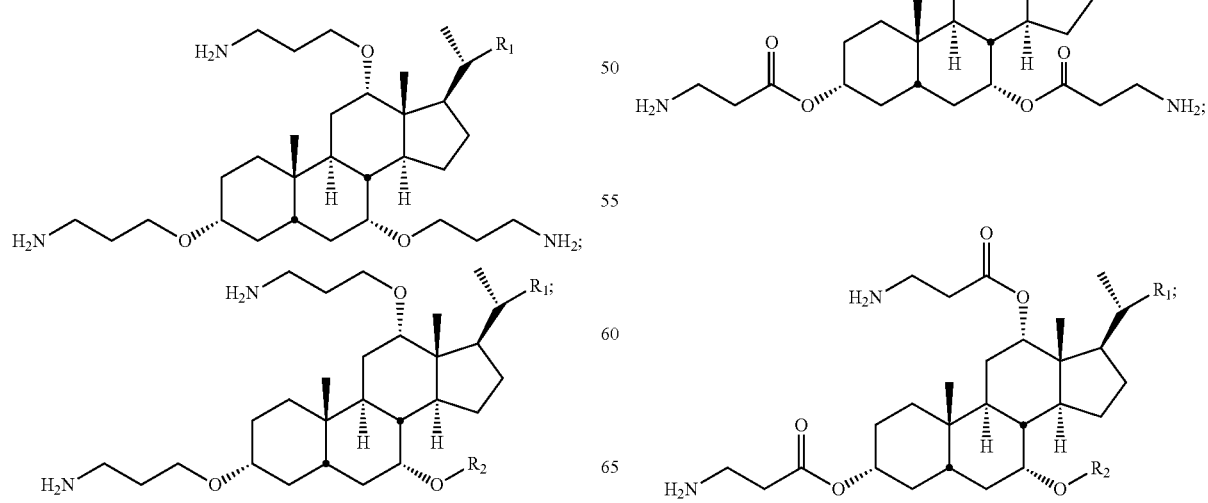

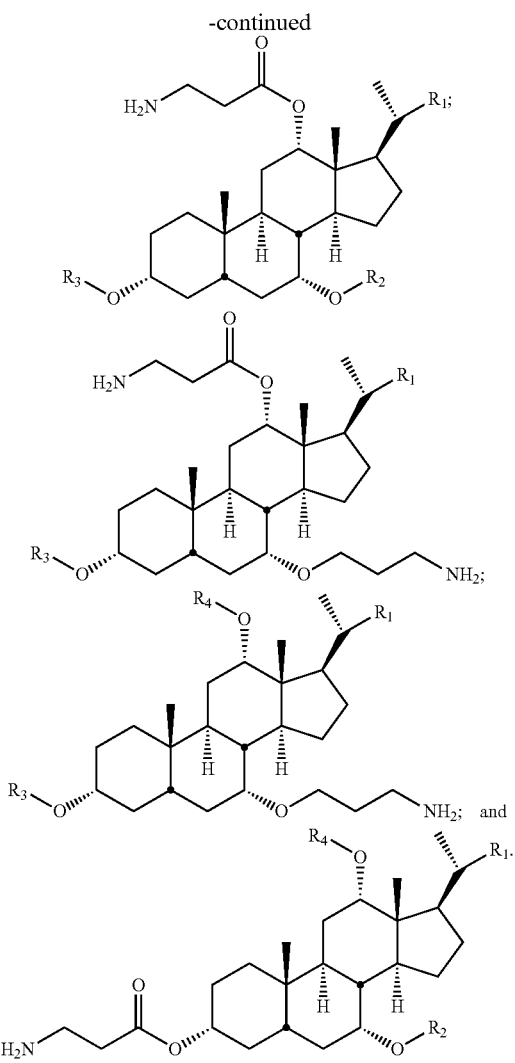

Some embodiments comprise a compound of Formula (I), or a pharmaceutically acceptable salt thereof, and a pharmaceutically acceptable excipient.

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. Some embodiments are directed to a sulfuric acid addition salt or sulfonic acid addition salt of a CSA. In some embodiments, the sulfonic acid addition salt is a disulfonic acid addition salt. In some embodiments, the sulfonic acid addition salt is a 1,5-naphthalenedisulfonic acid addition salt. In some embodiments, the acid addition salt is a mono-addition salt. In other embodiments, the acid addition salt is a di-addition salt. In other embodiments, the acid addition salt is a tetra-addition salt.

In some embodiments, the pharmaceutically acceptable salt is a benzoic acid salt. In other embodiments, the acid addition salt is a benzenesulphonic acid salt. In other embodiments, the acid addition salt is a citric acid salt. In other embodiments, the acid addition salt is a fumaric acid salt. In other embodiments, the acid addition salt is a galactaric acid (mucic acid) salt. In other embodiments, the acid addition salt is al-hydroxy-2-naphthoic acid salt. In other embodiments, the acid addition salt is a pamoic acid salt. In other embodiments, the acid addition salt is a phosphoric acid salt. In other embodiments, the acid addition salt is a succinic acid salt. In other embodiments, the acid addition salt is a L-tartaric acid salt.

Pharmaceutical Compositions

While it is possible for the compounds described herein to be administered alone, it may be preferable to formulate the compounds as pharmaceutical compositions (e.g., formulations). As such, in yet another aspect, pharmaceutical compositions useful in the methods and uses of the disclosed embodiments are provided. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may compr In some embodiments a therapeutically or prophylactically effective amount of at least one compound as described herein, together with one or more pharmaceutically acceptable excipients. Optionally, the pharmaceutical compositions may compr In some embodiments a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g. dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used. In some embodiments be used in the preparation of injectables.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA for administration in a wide variety of applications. In some embodiments, one or more CSA compounds are complexed with a protein. In some embodiments, one or more CSA compounds are complexed with a protein to increase the CSA compounds's half-life. In other embodiments, one or more CSA compounds are complexed with a protein to decrease the CSA compounds's toxicity. Albumin is a particularly preferred protein for complexation with a CSA compound. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA is about 18:1 or less, such as about 9:1 or less. In some embodiments, the CSA is coated with albumin.

Alternatively, or in addition, non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA is between about 8:1 and 1:1, preferably about 4:1. In some embodiments, the toxicity reducing compound is allantoin.

In some embodiments, a CSA composition is prepared utilizing one or more surfactants. In specific embodiments, the CSA is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In some embodiments, the one or more poloxamer surfactant in the composition has a molecular weight of about 3600 g/mol for the central hydrophobic chain of polyoxypropylene and has about 70% polyoxyethylene content. In some embodiments, the ratio of the one or more poloxamer to CSA is between about 50 to 1; about 40 to 1; about 30 to 1; about 20 to 1; about 10 to 1; about 5 to 1; about 1 to 1; about 1 to 10; about 1 to 20; about 1 to 30; about 1 to 40; or about 1 to 50. In other embodiments, the ratio of the one or more poloxamer to CSA is between 50 to 1; 40 to 1; 30 to 1; 20 to 1; 10 to 1; 5 to 1; 1 to 1; 1 to 10; 1 to 20; 1 to 30; 1 to 40; or 1 to 50. In some embodiments, the ratio of the one or more poloxamer to CSA is between about 50 to 1 to about 1 to 50. In other embodiments, the ratio of the one or more poloxamer to CSA is between about 30 to 1 to about 3 to 1. In some embodiments, the poloxamer is Pluronic F127.

The amount of poloxamer may be based upon a weight percentage of the composition. In some embodiments, the amount of poloxamer is about 10%, 15%, 20%, 25%, 30%, 35%, 40%, about any of the aforementioned numbers, or a range bounded by any two of the aforementioned numbers or the formulation. In some embodiments, the one or more poloxamer is between about 10% to about 40% by weight of a formulation administered to the patient. In some embodiments, the one or more poloxamer is between about 20% to about 30% by weight of the formulation. In some embodiments, the formulation contains less than about 50%, 40%, 30%, 20%, 10%, 5%, or 1% of CSA, or about any of the aforementioned numbers. In some embodiments, the formulation contains less than about 20% by weight of CSA.

The above described poloxamer formulations are particularly suited for the methods of treatment, device coatings, preparation of unit dosage forms (e.g., solutions, mouthwashes, injectables), etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition compr In some embodiments a therapeutically or prophylactically effective amount of a compound described herein, together with at least one pharmaceutically acceptable excipient selected from the group consisting of—medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition compr In some embodiments about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA compr In some embodiments a multimer (e.g., a dimer, trimer, tetramer, or higher order polymer). In some exemplary embodiments, the CSA compounds can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve an intended therapeutic effect.

Dosages

The formulations may, for convenience, be prepared or provided as a unit dosage form. Preparation techniques include bringing into association the active ingredient (e.g., CSA/ceragenin) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA/ceragenin) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA/ceragenin) moistened with an inert liquid diluent. The tablets may optionally be coated or scored and may be formulated so as to provide a slow or controlled release of the active ingredient therein.

Compounds (e.g., CSA compounds/ceragenins), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA/ceragenin). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSA compounds/ceragenins) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherw In some embodiments locally delivered. Localized delivery is characterized by higher concentrations of drug at the site of desired action (e.g., the tumor or organ to be treated) versus systemic concentrations of the drug. Well-known localized delivery forms can be used, including long-acting injections; infusion directly into the site of action; depot delivery forms; controlled or sustained delivery compositions; transdermal patches; infusion pumps; and the like. The CSA can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or d In some embodimentsases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a d In some embodimentsase, ameliorating symptoms, slowing d In some embodimentsase progression, reversing damage, or curing a din some embodimentsase.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The systemic daily dosage regimen for an adult human patient may be, for example, an oral dose of between 0.01 mg and 3000 mg of the active ingredient, preferably between 1 mg and 700 mg, e.g. 5 to 200 mg. In some embodiments, the daily dosage regimen is 1 mg, 5 mg, 10, mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, or about any of the aforementioned numbers or a range bounded by any two of the aforementioned numbers. The dosage may be a single one or a series of two or more given in the course of one or more days, as is needed by the subject. In some embodiments, the compounds will be administered for a period of continuous therapy, for example for a week or more, or for months or years. Doses tailored for particular types of cancers or particular patients can be selected based, in part, on the $GI_{50}$, TGI, and $LC_{50}$ values set forth in the Examples that follow. Particularly preferred formulations for oral dosage include tablet or solutions, particularly solutions compatible with IV administration or solutions compatible with oral administration/use.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 μg/mL, 0.1 μg/mL, 0.5 μg/mL, 1 μg/mL, 5 μg/mL, 10 μg/mL, 15 μg/mL, 20 μg/mL, 2 μg/mL, 30 μg/mL, 35 μg/mL, 40 μg/mL, 45 μg/mL, 50 μg/mL, 55 μg/mL, 60 μg/mL, 65 μg/mL, 70 μg/mL, 75 μg/mL, 80 μg/mL, 85 μg/mL, 90 μg/mL, 95 μg/mL, 100 μg/mL, a range bounded by any two of the aforementioned numbers, or about any of the aforementioned numbers and ranges. In some embodiments, the therapeutic dose is sufficient to establish plasma levels in the range of about 0.1 μg/mL to about 10 μg/mL. In other embodiments, the therapeutic dose is sufficient to establish plasma levels in the range of 1 μg/mL to 20 μg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of diseases or conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may compr In some embodiments administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, e.g., serially, whereas in simultaneous therapy, effective dosages of two or more active ingredients are administered together. Various sequences of intermittent combination therapy may also be used.

Co-Administration:

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers.

In some embodiments, one or more CSA/ceragenin are co-administered. In other embodiments, the co-administration of CSA/ceragenin accounts for their therapeutic benefit. In some embodiments, co-administration is concurrent.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA/ceragenin is selected by measuring a biomarker in the patient. The term biomarker includes, but is not limited to, genetic regulation, protein levels, RNA levels, and cellular responses such as cytotoxicity.

Methods and Uses:

CSA compounds/ceragenins have utility for known and new therapies and uses including, but not limited to anti-bacterial, anti-cancer, anti-inflammatory, bone growth, and wound healing. Moreover, many of the CSA compounds described herein exhibit one or more of the aforementioned properties as well as possess improved solution stability, lipophilicity, and favorable elution profiles and stabilities in various media, polymers, and hydrogels. Such properties are of critical concern for the handling and use of CSA compounds as pharmaceutical agents.

Synthesis of CSA Compounds:

Compounds described herein can be prepared by known methods. A skilled artisan will readily understand that minor variations of starting materials and reagents may be utilized to prepare known and novel cationic steroidal antimicrobials. For example, the preparation of CSA-131 can be used to prepare CSA-132 by using a $C_{18}$-alkylamine rather than a $C_{12}$-alkylamine as disclosed. Schematically, for example, the preparation of certain compounds can be accomplished according to Schemes 1 and 2 as follows:

Scheme 1: Ether-containing CSA Compounds

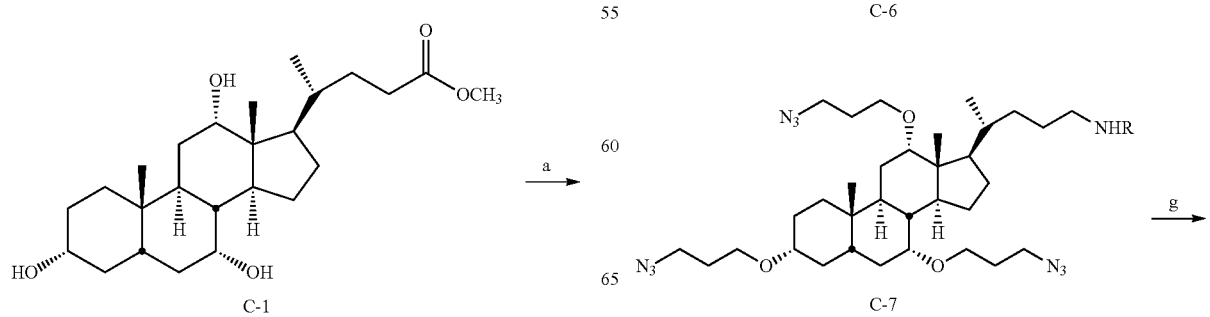

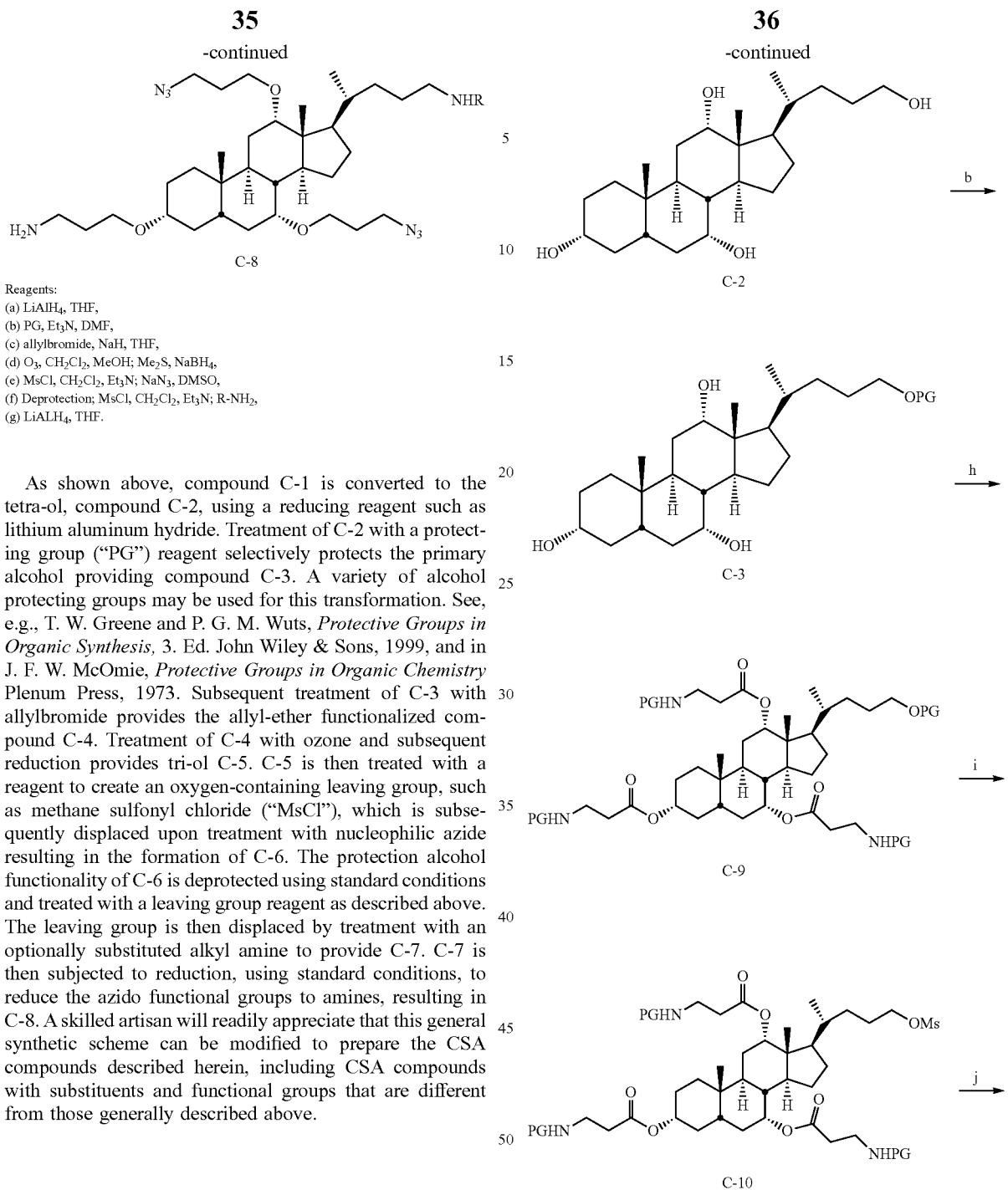

C-8

Reagents:
(a) LiAlH₄, THF,
(b) PG, Et₃N, DMF,
(c) allylbromide, NaH, THF,
(d) O₃, CH₂Cl₂, MeOH; Me₂S, NaBH₄,
(e) MsCl, CH₂Cl₂, Et₃N; NaN₃, DMSO,
(f) Deprotection; MsCl, CH₂Cl₂, Et₃N; R-NH₂,
(g) LiALH₄, THF.

As shown above, compound C-1 is converted to the tetra-ol, compound C-2, using a reducing reagent such as lithium aluminum hydride. Treatment of C-2 with a protecting group ("PG") reagent selectively protects the primary alcohol providing compound C-3. A variety of alcohol protecting groups may be used for this transformation. See, e.g., T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973. Subsequent treatment of C-3 with allylbromide provides the allyl-ether functionalized compound C-4. Treatment of C-4 with ozone and subsequent reduction provides tri-ol C-5. C-5 is then treated with a reagent to create an oxygen-containing leaving group, such as methane sulfonyl chloride ("MsCl"), which is subsequently displaced upon treatment with nucleophilic azide resulting in the formation of C-6. The protection alcohol functionality of C-6 is deprotected using standard conditions and treated with a leaving group reagent as described above. The leaving group is then displaced by treatment with an optionally substituted alkyl amine to provide C-7. C-7 is then subjected to reduction, using standard conditions, to reduce the azido functional groups to amines, resulting in C-8. A skilled artisan will readily appreciate that this general synthetic scheme can be modified to prepare the CSA compounds described herein, including CSA compounds with substituents and functional groups that are different from those generally described above.

Scheme 2: Ester-containing CSA Compounds

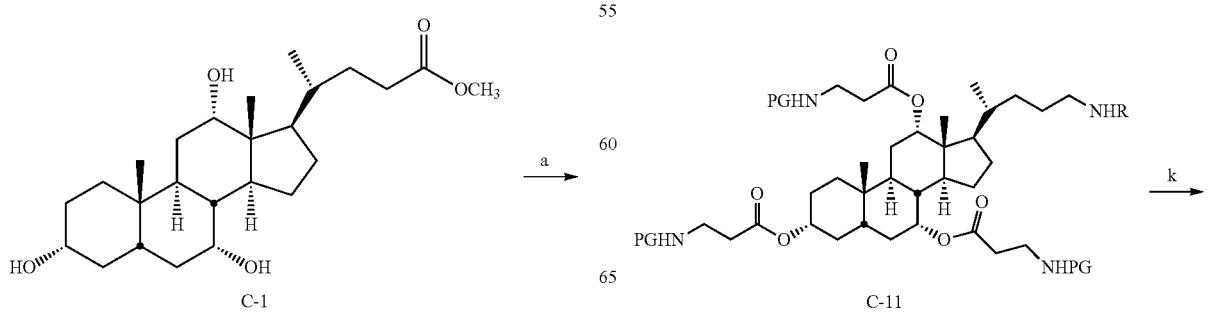

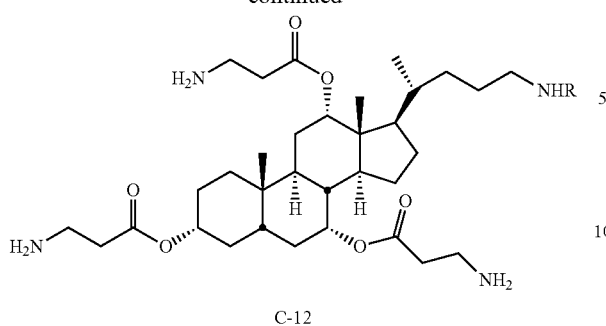

C-12

Reagents:
(a) LiAlH₄, THF,
(b) PG, Et₃N, DMF,
(h) 3-PG-aminopropanic acid, dicyclohexylcarbodiimide,
    N-hydroxysuccinimide, CH₂Cl₂, MeOH,
(i) Deprotection; MsCl, CH₂Cl₂, Et₃N,
(j) R-NH₂, CH₂Cl₂, Et₃N,
(k) Deprotection.

As shown above, compound C-1 is converted to the tetra-ol, compound C-2, using a reducing reagent such as lithium aluminum hydride. Treatment of C-2 with a protecting group ("PG") reagent selectively protects the primary alcohol providing compound C-3. A variety of alcohol protecting groups may be used for this transformation. See, e.g., T. W. Greene and P. G. M. Wuts, *Protective Groups in Organic Synthesis,* 3. Ed. John Wiley & Sons, 1999, and in J. F. W. McOmie, *Protective Groups in Organic Chemistry* Plenum Press, 1973. Compound C-3 is subsequently treated with esterification reagents [such as dicyclohexylcarbodiimide and N-hydroxysuccinimide, followed by 3-PG-aminopropanoic acid (the protected amine derivative of 3-aminopropanoic acid)] to provide compound C-9. Compound C-9 is deprotected using standard conditions and treated with a reagent to form a suitable leaving group (e.g. mesyl chloride) as described above, to provide C-10. Treatment of C-10 with an optionally substituted alkyl amine provides compound C-11, which is subjected to standard amine-deprotection conditions to provide CSA C-12.

Non-limiting examples of CSA compounds described in the present application are generally illustrated in the table below (wherein in this table, $C_{XX}$ indicates an unsubstituted, linear alkyl group having X carbon atoms). For example, —$C_2$ would represent ethyl or —$CH_2CH_3$; —$C_3$ would represent propyl or —$CH_2CH_2CH_3$, —$C_{12}$ would represent —$CH_2CH_2CH_2CH_2CH_2CH_2CH_2CH_2CH_2CH_2CH_2CH_3$; etc. A skilled artisan would also readily understand, as a further example, that an alternative representation of —$C_{12}$ would be —$(CH_2)_{11}CH_3$. These CSA compounds can be prepared according to Schemes 1 or 2 above.

CSA-131

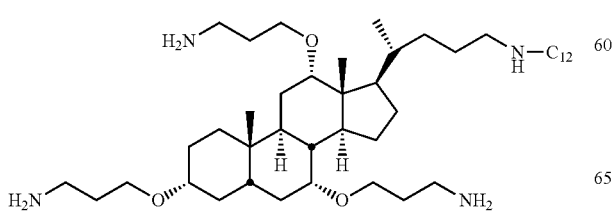

CSA-132

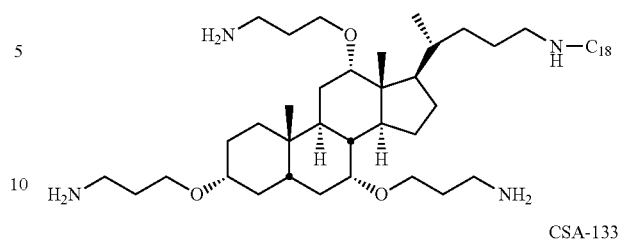

CSA-133

CSA-134

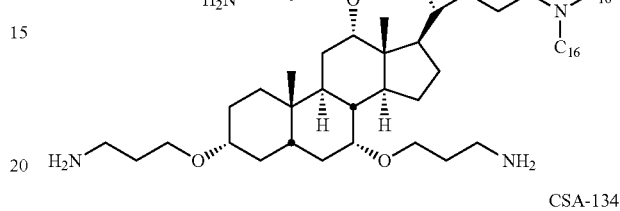

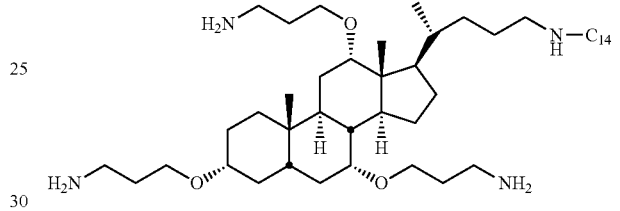

CSA-136

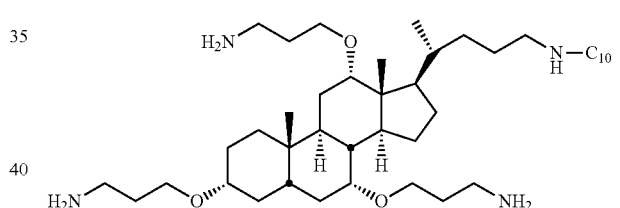

CSA-137

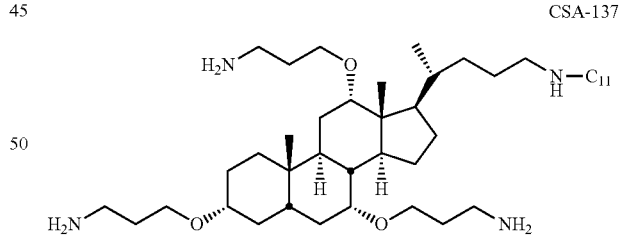

CSA-138

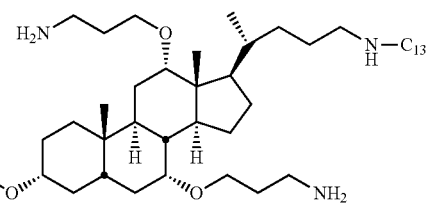

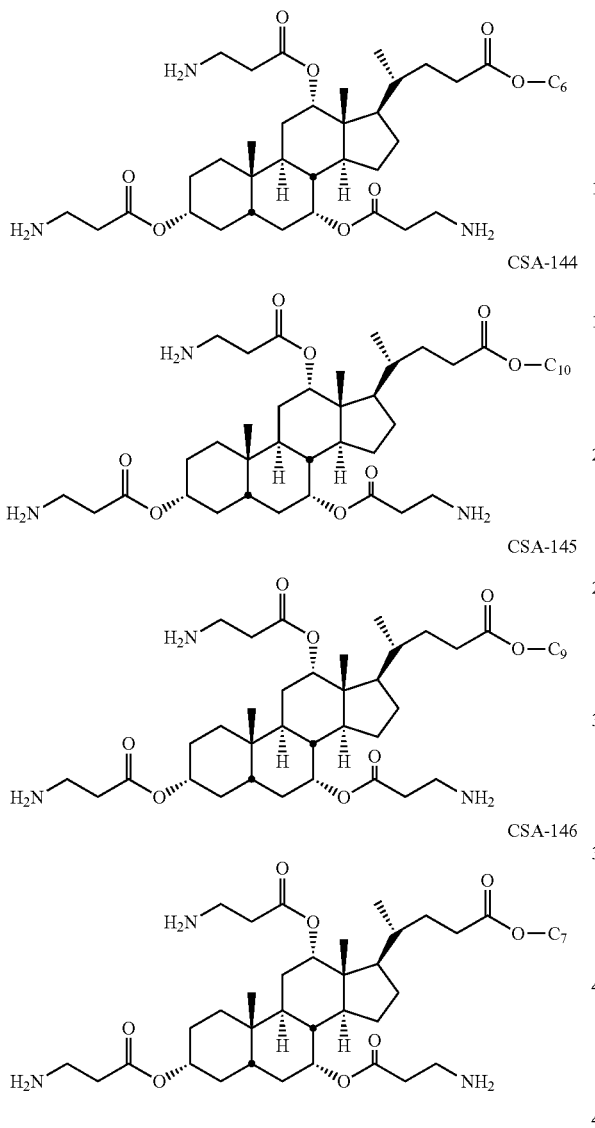
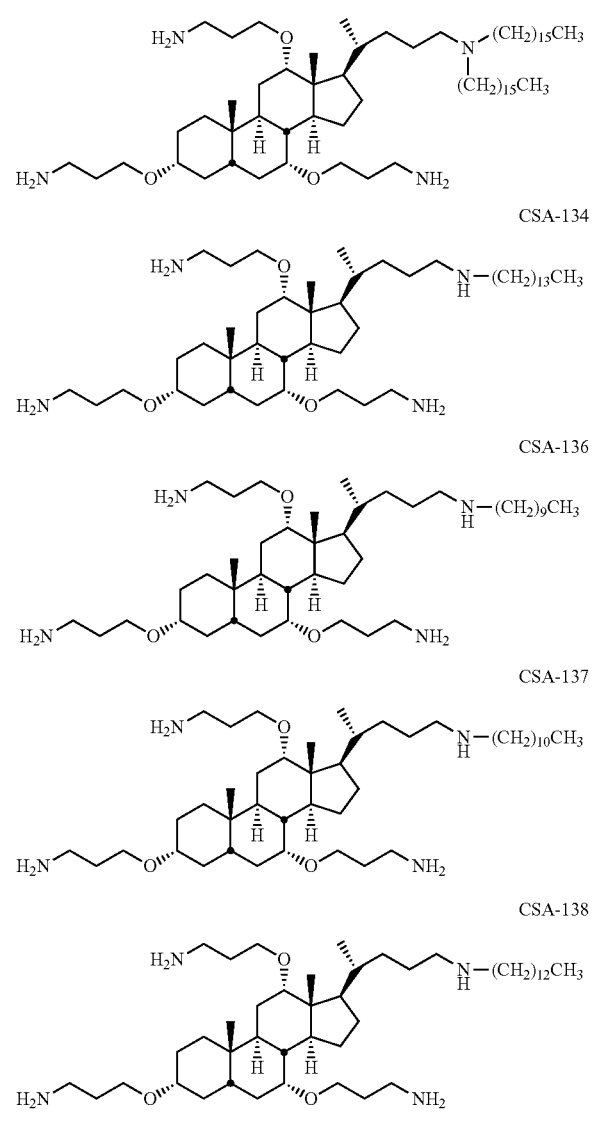
An alternative representation of these examples is as follows:
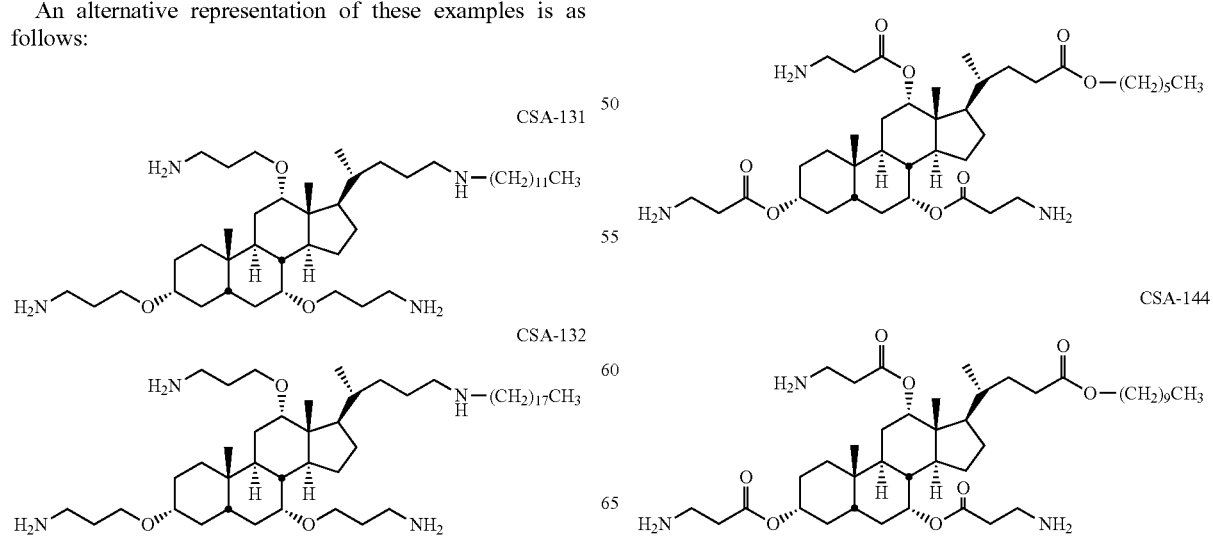

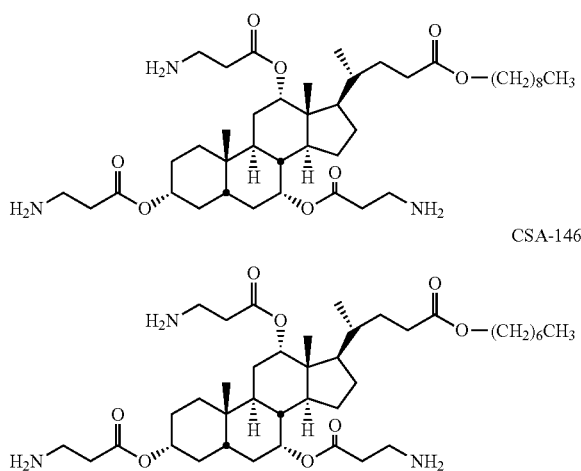

Using the above-described processes and procedures, additional CSA compounds generally and specifically described herein are synthesized and evaluated for their relative therapeutic efficacy.

Compounds of the invention and precursors to the compounds according to the invention are available commercially, e.g., from Sigm-Aldrich Co., St. Louis; MO; and Research Plus, Inc., Manasquan, N.J. Other compounds according to the invention can be synthesized according to methods disclosed herein and in the art.

Unless otherwise defined, all technical and scientific terms used herein have the same meaning as commonly understood by one of ordinary skill in the art to which this invention belongs. Although methods and materials similar or equivalent to those described herein can be used in the practice or study of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherw In some embodiments, disclosed features (e.g., compound structures) are an example of a genus of equivalent or similar features. All applications, publications, patents and other references, GenBank citations and ATCC citations cited herein are incorporated by reference in their entirety. In case of conflict, the specification, including definitions, will control.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 µg/kg, 1-10 µg/kg, 10-25 µg/kg, 25-50 µg/kg, 50-100 µg/kg, 100-500 µg/kg, 500-1,000 µg/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 µg/kg, 2-9 µg/kg, 11.5-24.5 µg/kg, 26-49 µg/kg, 55-90 µg/kg, 125-400 µg/kg, 750-800 µg/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc. A series of ranges, for example, 1-10 µg/kg, 10-25 µg/kg, 25-50 µg/kg, 50-100 µg/kg, 100-500 µg/kg, 500-1,000 µg/kg, 1-5 mg/kg, 5-10 mg/kg, 10-20 mg/kg, 20-50 mg/kg, 50-100 mg/kg, 100-250 mg/kg, 250-500 mg/kg, includes 1-25 µg/kg, 10-25 µg/kg, 25-100 µg/kg, 100-1,000 µg/kg, 1-10 mg/kg, 1-20 mg/kg etc.

The invention is generally disclosed herein using affirmative language to describe the numerous embodiments. The invention also includes embodiments in which subject matter is excluded, in full or in part, such as substances or materials, method steps and conditions, protocols, or procedures. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. For example, salts, esters, ethers and amides of invention compounds disclosed herein are within the scope of this invention. Accordingly, the following examples are intended to illustrate but not limit the scope of invention described in the claims.

Examples

Syntheses of CSA-131, 132, 134, and 136-138 followed the published procedures used to generate CSA-13 (Li, C.; Budge, L. P.; Driscoll, C. D.; Willardson, B. M.; Allman, G. W.; Savage, P. B. J. Am. Chem. Soc. 1999, 121, 931-940. Incremental conversion of outer-membrane permeabilizers into potent antibiotics for Gram-negative bacteria.) except that tetradecylamine, decylamine, undecylamine or tridecylamine was substituted for octylamine. Mass spectra showed the expected molecular ions for CSA-131, 132, 134, 136-138, and NMR spectra showed the expected resonances.

Syntheses of CSA-142 and 144-146 followed the published procedures used to generate CSA-44 (Guan, Q.; Schmidt, E. J.; Boswell, S. R.; Li, C.; Allman, G. W.; Savage, P. B. Org. Lett. 2000, 2, 2837-2840. Preparation and characterization of cholic acid-derived antimicrobial agents with controlled stabilities.) except that decanol, nonanol or heptanol was substituted for octanol. Mass spectra showed the expected molecular ions for CSA-142 and 144-146, and NMR spectra showed the expected resonances.

CONCLUSION

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

The invention claimed is:

1. A compound of Formula (I), or a pharmaceutically acceptable salt thereof:

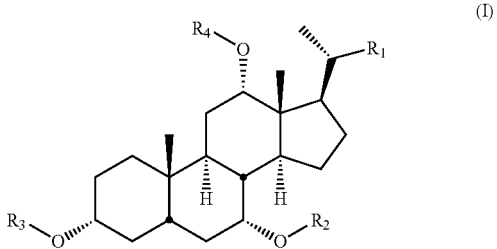

wherein,

R$_1$ is optionally substituted C$_{11-22}$-alkylester-C$_x$-alkyl;
R$_2$, R$_3$, and R$_4$, are independently selected from the group consisting of optionally substituted amino-C$_a$-alkyl and optionally substituted amino-C$_a$-alkylcarbonyl;
x is 1-5; and
a is 2-5.

2. The compound of Formula (I), or a pharmaceutically acceptable salt thereof, as in claim 1, wherein R$_1$ is an optionally substituted C$_{11}$-alkylester-C$_x$-alkyl.

3. The compound of Formula (I), or a pharmaceutically acceptable salt thereof, as in claim 1, wherein R$_1$ is an optionally substituted C$_{12-22}$-alkylester-C$_x$-alkyl.

4. The compound of Formula (I), or a pharmaceutically acceptable salt thereof, as in claim 1, wherein the ester is a carboxylic ester selected from oxycarbonyl or carbonyloxy.

5. The compound of Formula (I), or a pharmaceutically acceptable salt thereof, as in claim 1, wherein x is 2.

6. The compound of Formula (I), or a pharmaceutically acceptable salt thereof, as in claim 1, wherein x is 3.

7. The compound of Formula (I), or a pharmaceutically acceptable salt thereof, as in claim 1, wherein x is 4.

8. The compound of Formula (I), or a pharmaceutically acceptable salt thereof, as in claim 1, wherein x is 5.

9. The compound of Formula (I), or a pharmaceutically acceptable salt thereof, as in claim 1, wherein two or three of R$_2$, R$_3$, and R$_4$ are the same.

10. The compound of Formula (I), or a pharmaceutically acceptable salt thereof, as in claim 1, wherein R$_2$, R$_3$, and R$_4$ are all different.

11. The compound of Formula (I), or a pharmaceutically acceptable salt thereof, as in claim 1, wherein a is 2.

12. The compound of Formula (I), or a pharmaceutically acceptable salt thereof, as in claim 1, wherein a is 3.

13. The compound of Formula (I), or a pharmaceutically acceptable salt thereof, as in claim 1, wherein a is 4.

14. The compound of Formula (I), or a pharmaceutically acceptable salt thereof, as in claim 1, wherein a is 5.

15. The compound of Formula (I), or a pharmaceutically acceptable salt thereof, as in claim 1, wherein R$_2$, R$_3$, and R$_4$ are optionally substituted amino-C$_a$-alkyl.

16. The compound of Formula (I), or a pharmaceutically acceptable salt thereof, as in claim 1, wherein R$_2$, R$_3$, and R$_4$ are optionally substituted amino-C$_a$-alkylcarbonyl.

17. The compound of Formula (I), or a pharmaceutically acceptable salt thereof, as in claim 1, wherein one or more of R$_1$, R$_2$, R$_3$, and R$_4$ is unsubstituted.

18. The compound of Formula (I), or a pharmaceutically acceptable salt thereof, as in claim 1, wherein two or more of R$_1$, R$_2$, R$_3$, and R$_4$ are unsubstituted.

19. The compound of Formula (I), or a pharmaceutically acceptable salt thereof, as in claim 1, wherein three or more of R$_1$, R$_2$, R$_3$, and R$_4$ are unsubstituted.

20. The compound of Formula (I), or a pharmaceutically acceptable salt thereof, as in claim 1, wherein R$_1$, R$_2$, R$_3$, and R$_4$ are unsubstituted.

21. A pharmaceutical composition comprising at one compound of Formula (I), or a pharmaceutically acceptable salt thereof, as in claim 1 and a pharmaceutically acceptable excipient.

22. The pharmaceutical composition as in claim 21, wherein the pharmaceutically acceptable excipient is a liquid or a solid.

23. A composition of matter comprising at one compound of Formula (I), or a pharmaceutically acceptable salt thereof, as in claim 1 and at least one carrier.

24. The composition of matter as in claim 23, wherein the carrier is a liquid or a solid.

25. The compound of Formula (I), or a pharmaceutically acceptable salt thereof, as in claim 1 selected from the group consisting of:

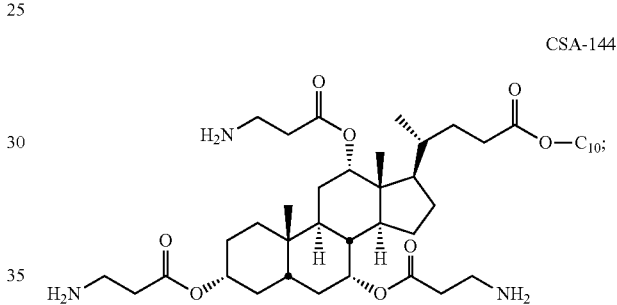

and pharmaceutically acceptable salts thereof.

26. The compound of Formula (I), or a pharmaceutically acceptable salt thereof, as in claim 1, wherein the pharmaceutically acceptable salt of the compound of Formula (I) is an acid addition salt of sulfuric acid, nitric acid, phosphoric acid, organic acid, carboxylic acid, or sulfonic acid.

27. The compound of Formula (I), or a pharmaceutically acceptable salt thereof, as in claim 1, wherein the pharmaceutically acceptable salt of the compound of Formula (I) is an acid addition of a carboxylic acid selected from the group consisting of formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, salicylic acid, stearic acid, muconic acid, butyric acid, phenylacetic acid, phenylbutyric acid, and valproic acid.

28. The compound of Formula (I), or a pharmaceutically acceptable salt thereof, as in claim 1, wherein the pharmaceutically acceptable salt of the compound of Formula (I) is an acid addition of a sulfonic acid selected from the group consisting of methanesulfonic acid, ethanesulfonic acid, p-toluensulfonic acid, 1,2-ethanedisulfonic acid, 2-hydroxyethanesulfonic acid, benzenesulfonic acid, 2-naphthalenesulfonic acid, and naphthalenesulfonic acid.

* * * * *

UNITED STATES PATENT AND TRADEMARK OFFICE
CERTIFICATE OF CORRECTION

PATENT NO. : 11,286,276 B2
APPLICATION NO. : 15/481884
DATED : March 29, 2022
INVENTOR(S) : Paul B. Savage et al.

It is certified that error appears in the above-identified patent and that said Letters Patent is hereby corrected as shown below:

In the Specification

Column 25
Lines 16-17, change "may compr In some embodiments" to – may comprise –

Column 25
Line 22, change "may compr In some embodiments" to – may comprise –

Column 28
Lines 59-60, change "compr In some embodiments" to – comprise –

Column 29
Line 10, change "compr In some embodiments" to – comprise –

Column 29
Lines 17-18, change "a CSA compr In some embodiments" to – a CSA comprises –

Column 30
Lines 59-60, delete "or otherw In some embodiments"

Column 31
Line 11, change "or d In some embodimentsases" to – or diseases –

Column 31
Line 26, change "d In some embodimentsase" to – disease –

Column 31
Line 27, change "d In some embodimentsase" to – disease –

Signed and Sealed this
Twenty-sixth Day of July, 2022

Katherine Kelly Vidal
*Director of the United States Patent and Trademark Office*

Column 31
Line 28, change "a din some embodimentsase" to – a disease –

Column 31
Line 56, change "for compounds" to – for CSA compounds –

Column 32
Line 62, change "compr In some embodiments" to – comprise –

Column 41
Line 44, change "otherw In some embodiments" to – otherwise –